United States Patent
Lesniewski et al.

(10) Patent No.: US 6,596,476 B1
(45) Date of Patent: *Jul. 22, 2003

(54) HEPATITIS C ASSAY

(75) Inventors: Richard R. Lesniewski, Kenosha, WI (US); Tat K. Leung, Waukegan, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 9 days.

(21) Appl. No.: 08/905,054

(22) Filed: Aug. 1, 1997

Related U.S. Application Data

(63) Continuation of application No. 08/707,355, filed on Sep. 4, 1996, now abandoned, which is a continuation of application No. 08/507,740, filed on Jul. 26, 1995, now abandoned, which is a continuation of application No. 08/373,920, filed on Jan. 17, 1995, now abandoned, which is a continuation of application No. 08/183,207, filed on Jan. 18, 1994, now abandoned, which is a continuation of application No. 07/760,292, filed on Sep. 16, 1991, now abandoned, which is a continuation-in-part of application No. 07/610,180, filed on Nov. 7, 1990, now abandoned, which is a continuation-in-part of application No. 07/456,162, filed on Dec. 22, 1989, now abandoned.

(51) Int. Cl.[7] .......................... C12Q 1/70; G01N 33/576
(52) U.S. Cl. ............................. 435/5; 436/518; 436/820
(58) Field of Search ............................. 435/5; 436/518, 436/820

(56) References Cited

U.S. PATENT DOCUMENTS

| | | | | | |
|---|---|---|---|---|---|
| 5,670,152 | A | * | 9/1997 | Weiner et al. | 424/189.1 |
| 5,756,312 | A | * | 5/1998 | Weiner et al. | |
| 5,856,437 | A | * | 1/1999 | Miyamura et al. | 530/350 |

FOREIGN PATENT DOCUMENTS

| | | | |
|---|---|---|---|
| EP | 419182 | * | 3/1991 |
| GB | 2099578 | * | 8/1982 |

OTHER PUBLICATIONS

Kuo et al., Science 244: 362–364, 1989.*
Kremsdorf et al., J. Gen. Virol. 72:2557–2561, 1991.*
Hijikata et al., Biochem. Biophys. Research Comm. 175(1): 220–228, 1991.*

* cited by examiner

*Primary Examiner*—Donna C. Wortman
(74) *Attorney, Agent, or Firm*—Dianne Casuto

(57) ABSTRACT

The present invention provides an improved assay for detecting the presence of an antibody to an HCV antigen in a sample by contacting the sample with at least one polypeptide containing at least one epitope of an HCV antigen. Preferred assay formats include a confirmatory assay, a combination assay, a synthetic polypeptide-based assay, an immunodot assay and a competition assay.

14 Claims, 7 Drawing Sheets

SEQUENCE LISTING

<160> NUMBER OF SEQ ID NOS: 30

<210> SEQ ID NO 1
<211> LENGTH: 75
<212> TYPE: PRT
<213> ORGANISM: Hepatitis C Virus

<400> SEQUENCE: 1

Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr
65                  70                  75

<210> SEQ ID NO 2
<211> LENGTH: 41
<212> TYPE: PRT
<213> ORGANISM: Hepatitis C Virus

<400> SEQUENCE: 2

Tyr Leu Pro Arg Arg Gly Pro Arg Leu Gly Val Arg Ala Thr Arg
1               5                   10                  15

Lys Thr Ser Glu Arg Ser Gln Pro Arg Gly Arg Arg Gln Pro Ile Pro
                20                  25                  30

Lys Ala Arg Arg Pro Glu Gly Arg Thr
                35              40

<210> SEQ ID NO 3
<211> LENGTH: 28
<212> TYPE: PRT
<213> ORGANISM: Hepatitis C Virus

<400> SEQUENCE: 3

Ser Pro Arg Gly Ser Arg Pro Ser Trp Gly Pro Thr Asp Pro Arg Arg
1               5                   10                  15

Arg Ser Arg Asn Leu Gly Lys Val Ile Asp Thr Leu
                20                  25

<210> SEQ ID NO 4
<211> LENGTH: 68
<212> TYPE: PRT
<213> ORGANISM: Hepatitis C Virus

<400> SEQUENCE: 4

Arg Asn Ser Thr Gly Leu Tyr His Val Thr Asn Asp Cys Pro Asn Ser
1               5                   10                  15

Ser Ile Val Tyr Glu Ala Ala Asp Ala Ile Leu His Thr Pro Gly Cys
                20                  25                  30

Val Pro Cys Val Arg Glu Gly Asn Ala Ser Arg Cys Trp Val Ala Met
            35                  40                  45

Thr Pro Thr Val Ala Thr Arg Asp Gly Lys Leu Pro Ala Thr Gln Leu
    50                  55                  60

Arg Arg His Ile
65

<210> SEQ ID NO 5
<211> LENGTH: 33
<212> TYPE: PRT
<213> ORGANISM: Hepatitis C Virus

<400> SEQUENCE: 5

Val Arg Glu Gly Asn Ala Ser Arg Cys Trp Val Ala Met Thr Pro Thr
1               5                   10                  15

Val Ala Thr Arg Asp Gly Lys Leu Pro Ala Thr Gln Leu Arg Arg His
                20                  25                  30

Ile

<210> SEQ ID NO 6
<211> LENGTH: 49
<212> TYPE: PRT
<213> ORGANISM: Hepatitis C Virus

<400> SEQUENCE: 6

Ala Val Asp Phe Ile Pro Val Glu Asn Leu Glu Thr Thr Met Arg Ser

```
                1               5                   10                  15
Pro Val Phe Thr Asp Asn Ser Pro Pro Val Val Pro Gln Ser Phe
                    20                  25                  30

Gln Val Ala His Leu His Ala Pro Thr Gly Ser Gly Lys Ser Thr Lys
                35                  40                  45

Val
```

<210> SEQ ID NO 7
<211> LENGTH: 18
<212> TYPE: PRT
<213> ORGANISM: Hepatitis C Virus

<400> SEQUENCE: 7

```
Phe Gln Val Ala His Leu His Ala Pro Thr Gly Ser Gly Lys Ser Thr
1               5                   10                  15

Lys Val
```

<210> SEQ ID NO 8
<211> LENGTH: 52
<212> TYPE: PRT
<213> ORGANISM: Hepatitis C Virus

<400> SEQUENCE: 8

```
Tyr Val Pro His Pro Asn Ile Glu Glu Val Ala Leu Ser Thr Thr Gly
1               5                   10                  15

Glu Ile Pro Phe Tyr Gly Lys Ala Ile Pro Leu Glu Val Ile Lys Gly
                20                  25                  30

Gly Arg His Leu Ile Phe Cys His Ser Lys Lys Lys Cys Asp Glu Leu
                35                  40                  45

Ala Ala Lys Leu
            50
```

<210> SEQ ID NO 9
<211> LENGTH: 39
<212> TYPE: PRT
<213> ORGANISM: Hepatitis C Virus

<400> SEQUENCE: 9

```
Arg Gly Leu Asp Val Ser Val Ile Pro Thr Ser Gly Asp Val Val Val
1               5                   10                  15

Val Ala Thr Asp Ala Leu Met Thr Gly Tyr Thr Gly Asp Phe Asp Ser
                20                  25                  30

Val Ile Asp Cys Asn Thr Cys
            35
```

<210> SEQ ID NO 10
<211> LENGTH: 25
<212> TYPE: PRT
<213> ORGANISM: Hepatitis C Virus

<400> SEQUENCE: 10

```
Asp Ala His Phe Leu Ser Gln Thr Lys Gln Ser Gly Glu Asn Leu Pro
1               5                   10                  15

Tyr Leu Val Ala Tyr Gln Ala Thr Val
                20                  25
```

<210> SEQ ID NO 11
<211> LENGTH: 67
<212> TYPE: PRT
<213> ORGANISM: Hepatitis C Virus

<400> SEQUENCE: 11

| Gly | Arg | Val | Val | Leu | Ser | Gly | Lys | Pro | Ala | Ile | Ile | Pro | Asp | Arg | Glu |
| --- | --- | --- | --- | --- | --- | --- | --- | --- | --- | --- | --- | --- | --- | --- | --- |
| 1 | | | | 5 | | | | | 10 | | | | | 15 | |

| Val | Leu | Tyr | Arg | Glu | Phe | Asp | Glu | Met | Glu | Glu | Cys | Ser | Gln | His | Leu |
| --- | --- | --- | --- | --- | --- | --- | --- | --- | --- | --- | --- | --- | --- | --- | --- |
| | | | 20 | | | | | 25 | | | | | 30 | | |

| Pro | Tyr | Ile | Glu | Gln | Gly | Met | Met | Leu | Ala | Glu | Gln | Phe | Lys | Gln | Lys |
| --- | --- | --- | --- | --- | --- | --- | --- | --- | --- | --- | --- | --- | --- | --- | --- |
| | | | 35 | | | | | 40 | | | | | 45 | | |

| Ala | Leu | Gly | Leu | Leu | Gln | Thr | Ala | Ser | Arg | Gln | Ala | Glu | Val | Ile | Ala |
| --- | --- | --- | --- | --- | --- | --- | --- | --- | --- | --- | --- | --- | --- | --- | --- |
| | 50 | | | | | 55 | | | | | 60 | | | | |

| Pro | Ala | Val |
| --- | --- | --- |
| 65 | | |

<210> SEQ ID NO 12
<211> LENGTH: 117
<212> TYPE: PRT
<213> ORGANISM: Hepatitis C Virus

<400> SEQUENCE: 12

| Ser | Gly | Lys | Pro | Ala | Ile | Ile | Pro | Asp | Arg | Glu | Val | Leu | Tyr | Arg | Glu |
| --- | --- | --- | --- | --- | --- | --- | --- | --- | --- | --- | --- | --- | --- | --- | --- |
| 1 | | | | 5 | | | | | 10 | | | | | 15 | |

| Phe | Asp | Glu | Met | Glu | Glu | Cys | Ser | Gln | His | Leu | Pro | Tyr | Ile | Glu | Gln |
| --- | --- | --- | --- | --- | --- | --- | --- | --- | --- | --- | --- | --- | --- | --- | --- |
| | | | 20 | | | | | 25 | | | | | 30 | | |

| Gly | Met | Met | Leu | Ala | Glu | Gln | Phe | Lys | Gln | Lys | Ala | Leu | Gly | Leu | Leu |
| --- | --- | --- | --- | --- | --- | --- | --- | --- | --- | --- | --- | --- | --- | --- | --- |
| | | | 35 | | | | | 40 | | | | | 45 | | |

| Gln | Thr | Ala | Ser | Arg | Gln | Ala | Glu | Val | Ile | Ala | Pro | Ala | Val | Gln | Thr |
| --- | --- | --- | --- | --- | --- | --- | --- | --- | --- | --- | --- | --- | --- | --- | --- |
| | 50 | | | | | 55 | | | | | 60 | | | | |

| Asn | Trp | Gln | Lys | Leu | Glu | Thr | Phe | Trp | Ala | Lys | His | Met | Trp | Asn | Phe |
| --- | --- | --- | --- | --- | --- | --- | --- | --- | --- | --- | --- | --- | --- | --- | --- |
| 65 | | | | | 70 | | | | | 75 | | | | | 80 |

| Ile | Ser | Gly | Ile | Gln | Tyr | Leu | Ala | Gly | Leu | Ser | Thr | Leu | Pro | Gly | Asn |
| --- | --- | --- | --- | --- | --- | --- | --- | --- | --- | --- | --- | --- | --- | --- | --- |
| | | | 85 | | | | | 90 | | | | | 95 | | |

| Pro | Ala | Ile | Ala | Ser | Leu | Met | Ala | Phe | Thr | Ala | Ala | Val | Thr | Ser | Pro |
| --- | --- | --- | --- | --- | --- | --- | --- | --- | --- | --- | --- | --- | --- | --- | --- |
| | | | 100 | | | | | 105 | | | | | 110 | | |

| Leu | Thr | Thr | Ser | Gln |
| --- | --- | --- | --- | --- |
| | | 115 | | |

<210> SEQ ID NO 13
<211> LENGTH: 42
<212> TYPE: PRT
<213> ORGANISM: Hepatitis C Virus

<400> SEQUENCE: 13

| Ile | Ile | Pro | Asp | Arg | Glu | Val | Leu | Tyr | Arg | Glu | Phe | Asp | Glu | Met | Glu |
| --- | --- | --- | --- | --- | --- | --- | --- | --- | --- | --- | --- | --- | --- | --- | --- |
| 1 | | | | 5 | | | | | 10 | | | | | 15 | |

| Glu | Cys | Ser | Gln | His | Leu | Pro | Tyr | Ile | Glu | Gln | Gly | Met | Met | Leu | Ala |
| --- | --- | --- | --- | --- | --- | --- | --- | --- | --- | --- | --- | --- | --- | --- | --- |
| | | | 20 | | | | | 25 | | | | | 30 | | |

| Glu | Gln | Phe | Lys | Gln | Lys | Ala | Leu | Gly | Leu |
| --- | --- | --- | --- | --- | --- | --- | --- | --- | --- |
| | | | 35 | | | | | 40 | |

<210> SEQ ID NO 14
<211> LENGTH: 65
<212> TYPE: PRT
<213> ORGANISM: Hepatitis C Virus

<400> SEQUENCE: 14

| Phe | Lys | Ile | Met | Ser | Gly | Glu | Val | Pro | Ser | Thr | Glu | Asp | Leu | Val | Asn |
| --- | --- | --- | --- | --- | --- | --- | --- | --- | --- | --- | --- | --- | --- | --- | --- |
| 1 | | | | 5 | | | | | 10 | | | | | 15 | |

| Leu | Leu | Pro | Ala | Ile | Leu | Ser | Pro | Gly | Ala | Leu | Val | Val | Gly | Val | Val |

-continued

```
                20                  25                  30
Cys Ala Ala Ile Leu Arg Arg His Val Gly Pro Gly Glu Gly Ala Val
            35                  40                  45
Gln Trp Met Asn Arg Leu Ile Ala Phe Ala Ser Arg Gly Asn His Val
    50                  55                  60
Ser
65

<210> SEQ ID NO 15
<211> LENGTH: 32
<212> TYPE: PRT
<213> ORGANISM: Hepatitis C Virus

<400> SEQUENCE: 15

Ala Ala Ile Leu Arg Arg His Val Gly Pro Gly Glu Gly Ala Val Gln
1               5                   10                  15
Trp Met Asn Arg Leu Ile Ala Phe Ala Ser Arg Gly Asn His Val Ser
                20                  25                  30

<210> SEQ ID NO 16
<211> LENGTH: 57
<212> TYPE: PRT
<213> ORGANISM: Hepatitis C Virus

<400> SEQUENCE: 16

Gly Val Asp Ala Glu Thr His Val Thr Gly Gly Ser Ala Gly His Thr
1               5                   10                  15
Val Ser Gly Phe Val Ser Leu Leu Ala Pro Gly Ala Lys Gln Asn Val
                20                  25                  30
Gln Leu Ile Asn Thr Asn Gly Ser Trp His Leu Asn Ser Thr Ala Leu
            35                  40                  45
Asn Cys Asn Asp Ser Ser Asn Thr Gly
    50                  55

<210> SEQ ID NO 17
<211> LENGTH: 57
<212> TYPE: PRT
<213> ORGANISM: Hepatitis C Virus

<400> SEQUENCE: 17

Gly Val Asp Ala Ala Thr Tyr Thr Thr Gly Gly Ser Val Ala Arg Thr
1               5                   10                  15
Thr His Gly Phe Ser Ser Leu Phe Ser Gln Gly Ala Lys Gln Asn Ile
                20                  25                  30
Gln Leu Ile Asn Thr Asn Gly Ser Trp His Ile Asn Arg Thr Ala Leu
            35                  40                  45
Asn Cys Asn Ala Ser Leu Asp Thr Gly
    50                  55

<210> SEQ ID NO 18
<211> LENGTH: 37
<212> TYPE: PRT
<213> ORGANISM: Hepatitis C Virus

<400> SEQUENCE: 18

Phe Asn Ser Ser Gly Cys Pro Glu Arg Leu Ala Ser Cys Arg Pro Leu
1               5                   10                  15
Thr Asp Phe Asp Gln Gly Trp Gly Pro Ile Ser Tyr Ala Asn Gly Ser
                20                  25                  30
```

```
Gly Pro Asp Gln Arg
        35

<210> SEQ ID NO 19
<211> LENGTH: 21
<212> TYPE: PRT
<213> ORGANISM: Hepatitis C Virus

<400> SEQUENCE: 19

Cys Leu Val Asp Tyr Pro Tyr Arg Leu Trp His Tyr Pro Cys Thr Ile
 1               5                  10                  15

Asn Tyr Thr Ile Phe
            20

<210> SEQ ID NO 20
<211> LENGTH: 22
<212> TYPE: PRT
<213> ORGANISM: Artificial Sequence
<220> FEATURE:
<223> OTHER INFORMATION: Modified Peptides

<400> SEQUENCE: 20

Ala Cys Asn Trp Thr Arg Gly Glu Arg Cys Asp Leu Glu Asp Arg Asp
 1               5                  10                  15

Arg Ser Glu Leu Ser Tyr
            20

<210> SEQ ID NO 21
<211> LENGTH: 41
<212> TYPE: PRT
<213> ORGANISM: Hepatitis C Virus

<400> SEQUENCE: 21

Ala Cys Asn Trp Thr Arg Gly Glu Arg Cys Asp Leu Glu Asp Arg Asp
 1               5                  10                  15

Arg Ser Glu Leu Ser Pro Leu Leu Leu Thr Thr Thr Gln Trp Gln Val
            20                  25                  30

Leu Pro Cys Ser Phe Thr Thr Leu Pro
        35                  40

<210> SEQ ID NO 22
<211> LENGTH: 19
<212> TYPE: PRT
<213> ORGANISM: Artificial Sequence
<220> FEATURE:
<223> OTHER INFORMATION: Modified Peptides

<400> SEQUENCE: 22

Leu Leu Thr Thr Thr Gln Trp Gln Val Leu Pro Cys Ser Phe Thr Thr
 1               5                  10                  15

Leu Pro Tyr

<210> SEQ ID NO 23
<211> LENGTH: 24
<212> TYPE: PRT
<213> ORGANISM: Hepatitis C Virus

<400> SEQUENCE: 23

His Leu His Gln Asn Ile Val Asp Val Gln Tyr Leu Tyr Gly Val Gly
 1               5                  10                  15

Ser Ser Ile Ala Ser Trp Ala Ile
            20
```

<210> SEQ ID NO 24
<211> LENGTH: 51
<212> TYPE: PRT
<213> ORGANISM: Hepatitis C Virus

<400> SEQUENCE: 24

Lys Lys Pro Asp Tyr Gln Pro Pro Val Val His Gly Cys Pro Leu Pro
1               5                   10                  15

Pro Pro Lys Ser Pro Pro Val Pro Pro Lys Lys Lys Arg Thr Val
            20                  25                  30

Val Leu Thr Glu Ser Thr Leu Ser Thr Ala Leu Ala Glu Leu Ala Thr
            35                  40                  45

Arg Ser Phe
    50

<210> SEQ ID NO 25
<211> LENGTH: 57
<212> TYPE: PRT
<213> ORGANISM: Hepatitis C Virus

<400> SEQUENCE: 25

Gly Val Asp Gly His Thr Arg Val Thr Gly Gly Val Gln Gly His Val
1               5                   10                  15

Thr Ser Thr Leu Thr Ser Leu Phe Arg Pro Gly Ala Ser Gln Lys Ile
            20                  25                  30

Gln Leu Val Asn Thr Asn Gly Ser Thr His Ile Asn Arg Thr Ala Leu
            35                  40                  45

Asn Ser Asn Asp Ser Leu Gln Thr Gly
    50                  55

<210> SEQ ID NO 26
<211> LENGTH: 57
<212> TYPE: PRT
<213> ORGANISM: Hepatitis C Virus

<400> SEQUENCE: 26

Gly Val Asp Gly His Thr His Val Thr Gly Gly Arg Val Ala Ser Ser
1               5                   10                  15

Thr Gln Ser Leu Val Ser Trp Leu Ser Gln Gly Pro Ser Gln Lys Ile
            20                  25                  30

Gln Leu Val Asn Thr Asn Gly Ser Gln His Ile Asn Arg Thr Ala Leu
            35                  40                  45

Asn Cys Asn Asp Ser Leu Gln Thr Gly
    50                  55

<210> SEQ ID NO 27
<211> LENGTH: 29
<212> TYPE: PRT
<213> ORGANISM: Hepatitis C Virus

<400> SEQUENCE: 27

Ser Gln Lys Ile Gln Leu Val Asn Thr Asn Gly Ser Trp His Ile Asn
1               5                   10                  15

Arg Thr Ala Leu Asn Cys Asn Asp Ser Leu Gln Thr Gly
            20                  25

<210> SEQ ID NO 28
<211> LENGTH: 225
<212> TYPE: DNA
<213> ORGANISM: Hepatitis C Virus

```
<400> SEQUENCE: 28
atgtctacca acccgaaacc gcagaaaaaa aacaaacgta acaccaaccg tcgtccgcag      60
gacgttaaat tcccgggtgg tggtcagatc gttggtggtg tttacctgct gccgcgtcgt    120
ggtccgcgtc tgggtgttcg tgctacccgt aaaacctctg aacgttctca gccgcgtggt    180
cgtcgtcagc cgatcccgaa agctcgtcgt ccggaaggtc gtacc                    225

<210> SEQ ID NO 29
<211> LENGTH: 54
<212> TYPE: DNA
<213> ORGANISM: Hepatitis C Virus

<400> SEQUENCE: 29
ttccaggttg ctcacctgca cgctccgacc ggttctggta aatctaccaa agtt           54

<210> SEQ ID NO 30
<211> LENGTH: 201
<212> TYPE: DNA
<213> ORGANISM: Hepatitis C Virus

<400> SEQUENCE: 30
ggtcgtgttg ttctgtctgg taaaccggct atcatcccgg accgtgaagt tctgtaccgt     60
gaattcgacg aaatggaaga atgctctcag cacctgccgt acatcgaaca gggtatgatg    120
ctggctgaac agttcaaaca gaaagctctg ggtctgctgc agaccgcttc tcgtcaggct    180
gaagttatcg ctccggctgt t                                              201
```

HEPATITIS C ASSAY

This application is a continuation of application Ser. No. 08/707,355, filed Sep. 4, 1996, abandoned, which is a continuation of application Ser. No. 08/507,740, filed Jul. 26, 1995, abandoned, which is a continuation of application Ser. No. 08/373,920, filed Jan. 17, 1995, abandoned, which is a continuation of application Ser. No. 08/183,207, filed Jan. 18, 1994, abandoned, which is a continuation of application Ser. No. 07/760,292, filed Sep. 16, 1991, abandoned, which is a continuation-in-part of application Ser. No. 07/610,180, filed Nov. 7, 1990, abandoned, which is a continuation-in-part of application Ser. No. 07/456,162, filed Dec. 22, 1989, abandoned.

BACKGROUND OF THE INVENTION

This invention relates generally to an assay for identifying the presence and/or amount in a test sample of an antibody which is immunologically reactive with a hepatitis C viral antigen and more specifically, to an assay for detecting a complex of an antibody and a polypeptide having at least one epitope of a hepatitis C viral antigen.

Acute viral hepatitis is clinically diagnosed by a well-defined set of patient symptoms, including jaundice, hepatic tenderness, and an increase in the serum levels of alanine aminotransferase and aspartate aminotransferase. Additional serological immunoassays are generally performed to diagnose the specific type of viral causative agent. Historically, patients presenting clinical hepatitis symptoms and not otherwise infected by hepatitis A, hepatitis B, Epstein-Barr, or cytomegalovirus were clinically diagnosed as having non-A, non-B hepatitis (NANBH) by default. The disease may result in chronic liver damage.

Each of the well-known, immunologically characterized hepatitis-inducing viruses, hepatitis A virus (HAV), hepatitis B virus (HBV), and hepatitis D virus (HDV) belongs to a separate family of viruses and has a distinctive viral organization, protein structure and mode of replication.

Attempts to identify the NANBH virus by virtue of genomic similarity to one of the known hepatitis viruses have failed, suggesting that NANBH has a distinct organization and structure. Fowler et al., *J. Med. Virol.* 12:205–213 (1983) and Weiner et al., *J. Med. Virol.* 21:239–247 (1987).

Progress in developing assays to detect antibodies specific for NANBH has been particularly hampered by difficulties in correctly identifying antigens associated with NANBH. See, for example, J. Wands et al., U.S. Pat. No. 4,870,076, Wands et al., *Proc. Nat'l. Acad. Sci.* 83:6608–6612 (1986), Ohori et al., *J. Med. Virol.* 12:161–178 (1983), Bradley et al., *Proc. Nat'l. Acad. Sci.* 84:6277–6281 (1987), T. Akatsuka et al., *J. Med. Virol.* 20:43–56 (1986), B. Seto et al., U.S. patent application Ser. No. 07/234,641 (available from U.S. Department of Commerce National Technical Information Service, Springfield, Va. No. 89138168), K. Takahashi et al., European Patent Application No. 0 293 274, published Nov. 30, 1988, and R. Seelig et al., PCT Application PCT/EP88/00123.

Recently, another hepatitis-inducing virus has been unequivocally identified as hepatitis C virus (HCV) by M. Houghton et al., European Patent Application publication number 0 318 216, May 31, 1989. Related papers describing this virus include G. Kuo et al., *Science* 244:359–361 (1989) and Q. Choo et al., *Science* 244:362–364 (1989). M. Houghton et al. reported isolating cDNA sequences from HCV which encode antigens which react immunologically with antibodies present in patients infected with NANBH, thus establishing that HCV is the viral agent causing NANBH.

The CDNA sequences associated with HCV were isolated from a cDNA library prepared from the RNA obtained from pooled serum from a chimpanzee with chronic HCV infection. The cDNA library contained cDNA sequences of approximate mean size of about 200 base pairs. The cDNA library was screened for encoded epitopes expressed in clones that could bind to antibodies in sera from patients who had previously experienced NANBH.

In the European Patent Application, M. Houghton et al. also described the preparation of several superoxide dismutase fusion polypeptides (SOD) and the use of these SOD fusion polypeptides to develop an HCV screening assay. The most complex SOD fusion polypeptide described in the European Patent Application, designated C100-3, was described as containing 154 amino acids of human SOD at the amino-terminus, 5 amino acid residues derived from the expression of a synthetic DNA adapter containing a restriction site, EcoRI, 363 amino acids derived from the expression of a cloned HCV cDNA fragment, and 5 carboxy terminal amino acids derived from an MS2 cloning vector nucleotide sequence. The DNA sequence encoding this polypeptide was transformed into yeast cells using a plasmid. The transformed cells were cultured and expressed a 54,000 molecular weight polypeptide which was purified to about 80% purity by differential extraction.

Other SOD fusion polypeptides designated SOD-NANB$_{5-1-1}$ and SOD-NANB$_{81}$ were expressed in recombinant bacteria. The *E. coli* fusion polypeptides were purified by differential extraction and by chromatography using anion and cation exchange columns. The purification procedures were able to produce SOD-NANB$_{5-1-1}$ as about 80% pure and NANBH$_{81}$ as about 50% pure.

The recombinant SOD fusion polypeptides described by M. Houghton et al. were coated on microtiter wells or polystyrene beads and used to assay serum samples. Briefly, coated microtiter wells were incubated with a sample in a diluent. After incubation, the microtiter wells were washed and then developed using either a radioactively labelled sheep anti-human antibody or a mouse anti-human IgG-HRP (horseradish peroxidase) conjugate. These assays were used to detect both post acute phase and chronic phase of HCV infection. Due to the preparative methods, assay specificity required adding yeast or *E. coli* extracts to the samples in order to prevent undesired immunological reactions with any yeast or *E. coli* antibodies present in serum samples.

Ortho Diagnostics Systems Inc. have developed a research immunoenzyme assay to detect antibodies to HCV antigens. The Ortho assay procedure is a three-stage test for serum/plasma carried out in a microwell coated with the recombinant yeast/hepatitis C virus SOD fusion polypeptide C100-3.

In the first stage, a test specimen is diluted directly in the test well and incubated for a specified length of time. If antibodies to HCV antigens are present in the specimen, antigen-antibody complexes will be formed on the microwell surface. If no antibodies are present, complexes will not be formed, and the unbound serum or plasma proteins will be removed in a washing step.

In the second stage, anti-human IgG murine monoclonal antibody horseradish peroxidase conjugate is added to the microwell. The conjugate binds specifically to the antibody portion of the antigen-antibody complexes. If antigen-antibody complexes are not present, the unbound conjugate will also be removed by a washing step.

In the third stage, an enzyme detection system composed of o-phenylenediamine 2 HCl (OPD) and hydrogen peroxide is added to the test well. If bound conjugate is present, the OPD will be oxidized, resulting in a colored end product. After formation of the colored end product, dilute sulfuric acid is added to the microwell to stop the color-forming detection reaction.

The intensity of the colored end product is measured with a microwell reader. The assay may be used to screen patient serum and plasma.

It is established that HCV may be transmitted by contaminated blood and blood products. In transfusion patients, as many as 10% will suffer from post-transfusion hepatitis. Of those, approximately 90% are the result of infections diagnosed as HCV. The prevention of transmission of HCV by blood and blood products requires reliable, sensitive and specific diagnosis and prognostic tools to identify HCV carriers as well as contaminated blood and blood products. Thus, there exists a need for an HCV assay which uses reliable and efficient reagents and methods to accurately detect the presence of HCV antibodies in samples.

SUMMARY OF THE INVENTION

The present invention provides an improved assay for detecting the presence of an antibody to an HCV antigen in a test sample by contacting the sample with a polypeptide containing at least one epitope of an HCV antigen, wherein the polypeptides are selected from the group consisting of p380-JH1, p-380.LG, p380-J and p408.

One assay format according to the invention provides a confirmatory assay for unequivocally identifying the presence of an antibody that is immunologically reactive with an HCV antigen. Briefly, a fluid sample is used to prepare first and second aliquots. The aliquots then are contacted with at least two polypeptides duplicative of a continuous amino acid sequence putatively contained in proteins expressed by clones containing HCV cDNA sequences containing at least one epitope of an HCV antigen under conditions suitable for complexing the antibody with the polypeptide. Finally, the antibody-antigen complex is detected. The first aliquot and the second aliquot are contacted with at least one polypeptide selected from the group consisting of p380-JH1, p-380.LG, p380-J and p408J, with the proviso that the polypeptide(s) used for the first aliquot are not used for the second aliquot.

Another assay format provides an assay for identifying the presence of an antibody that is immunologically reactive with an HCV antigen in a fluid sample comprising contacting the sample with a solid phase having bound thereto at least one polypeptide selected from the group consisting of p380JH1, p380J, p380.LG and p408J containing at least one epitope of an HCV antigen, under conditions suitable for complexing the antibody with the polypeptide and detecting the antibody-polypeptide complex.

Another assay format provides an assay for identifying the presence of an antibody that is immunologically reactive with an HCV antigen in a fluid sample comprising contacting the sample with a polypeptide selected from the group consisting of p380JH1, p380J, p380.LG and p408J containing at least one epitope of an HCV antigen under conditions suitable for complexing the antibody with the polypeptide and detecting the antibody-polypeptide complex as an indication of chronic HCV infection.

Another assay format provides an immunodot assay for identifying the presence of an antibody that is immunologically reactive with an HCV antigen by concurrently contacting a sample with at least two polypeptides selected from the group consisting of p380JH1, p380J, p380.LG and p408J each containing distinct epitopes of an HCV antigen under conditions suitable for complexing the antibody with at least one of the polypeptides and detecting the antibody-polypeptide complex by reacting the complex with color-producing reagents.

Another assay format provides a competition assay directed to the confirmation that positive results are not false by identifying the presence of an antibody that is immunologically reactive with an HCV antigen in a fluid sample where the sample is used to prepare first and second immunologically equivalent aliquots. The first aliquot is contacted with a solid support containing a bound polypeptide selected from the group consisting of p380JH1, p380J, p380.LG and p408J which contains at least one epitope of an HCV antigen under conditions suitable for complexing with the antibody to form a detectable antibody-polypeptide complex and the second aliquot is first contacted with unbound polypeptide selected from the group consisting of p380JH1, p380J, p380.LG and p408J and then contacted with the same solid support containing bound polypeptide selected from the group consisting of p380JH1, p380J, p380.LG and p408J.

In all of the assays, the sample, especially serum or plasma, preferably is diluted before contacting the polypeptide absorbed on a solid support. However, it is contemplated that when testing some test samples, an undiluted or even concentrated sample may be preferred. Samples may be obtained from different biological samples such as whole blood, serum, plasma, cerebrospinal fluid, urine, and lymphocytes or cell culture supernatants. Solid support materials may include cellulose materials, such as paper and nitrocellulose, natural and synthetic polymeric materials, such as polyacrylamide, polystyrene, and cotton, silicon chips, porous gels such as silica gel, agarose, dextran and gelatin, particles which are capable of forming a charge such as those used for ion capture assays and inorganic materials such as deactivated alumina, magnesium sulfate and glass. Suitable solid support materials may be used in assays in a variety of well known physical configurations, including microtiter wells, test tubes, beads, strips, membranes, and microparticles, either magnetic or non-magnetic. A preferred solid support for a non-immunodot assay is a polystyrene bead. A preferred solid support for an immunodot blot assay is nitrocellulose.

Suitable methods and reagents for detecting an antibody-antigen complex in an assay of the present invention are commercially available or known in the relevant art. Representative methods may employ detection reagents such an enzymatic, radioisotopic, fluorescent, luminescent or chemiluminescent reagents. These reagents may be used to prepare hapten-labelled anti-hapten detection systems according to known procedures, for example, a biotin-labelled anti-biotin system may be used to detect an antibody-antigen complex.

The present invention also encompasses assay kits including polypeptides which contain at least one epitope of an HCV antigen bound to a solid support as well as needed sample preparation reagents, wash reagents, detection reagents and signal producing reagents.

Other aspects and advantages of the invention will be apparent to those skilled in the art upon consideration of the following detailed description which provides illustrations of the invention in its presently preferred embodiments.

DETAILED DESCRIPTION OF THE INVENTION

The present invention is directed to an assay to detect an antibody to an HCV antigen in a test sample. In a preferred format, human serum or plasma is diluted in a sample diluent and incubated with a polystyrene bead coated with a polypeptide that includes an HCV antigenic epitope. If antibodies are present in the sample, they will form a complex with the antigenic polypeptide and become affixed to the polystyrene bead. After the complex has formed, unbound materials and reagents are removed by washing the bead and the bead-antigen-antibody complex is reacted with a solution containing horseradish peroxidase labelled goat antibodies directed against human antibodies. This peroxidase enzyme then binds to the antigen-antibody complex already fixed to the bead. In a final reaction, the horseradish peroxidase is contacted with o-phenylenediamine and hydrogen peroxidase, which results in a yellow-orange color. The intensity of the color is proportional to the amount of antibody which initially binds to the antigen fixed to the bead.

The preferred polypeptides having HCV antigenic epitopes were selected from portions which possessed amino acid sequences similar to other known immunologically reactive agents and which were identified as having some immunological reactivity. The immunological reactivity of a polypeptide was initially identified by reacting the cellular extract of $E.\ coli$ clones which had been transformed with cDNA fragments of the HCV genome with HCV infected serum. The clones presumably expressed polypeptides encoded by the incorporated cDNA which were immunologically reactive with serum known to contain antibody to HCV antigens. An analysis of a given amino acid sequence, however, only provides rough guides to predicting immunological reactivity. There is no invariably predictable way to ensure immunological activity short of preparing a given amino acid sequence and testing the suspected sequence in an assay. As illustrated in Table 1, some peptides which were expected to provide immunological reactivity were found to be unreactive when used in an actual assay.

Figure 1A:
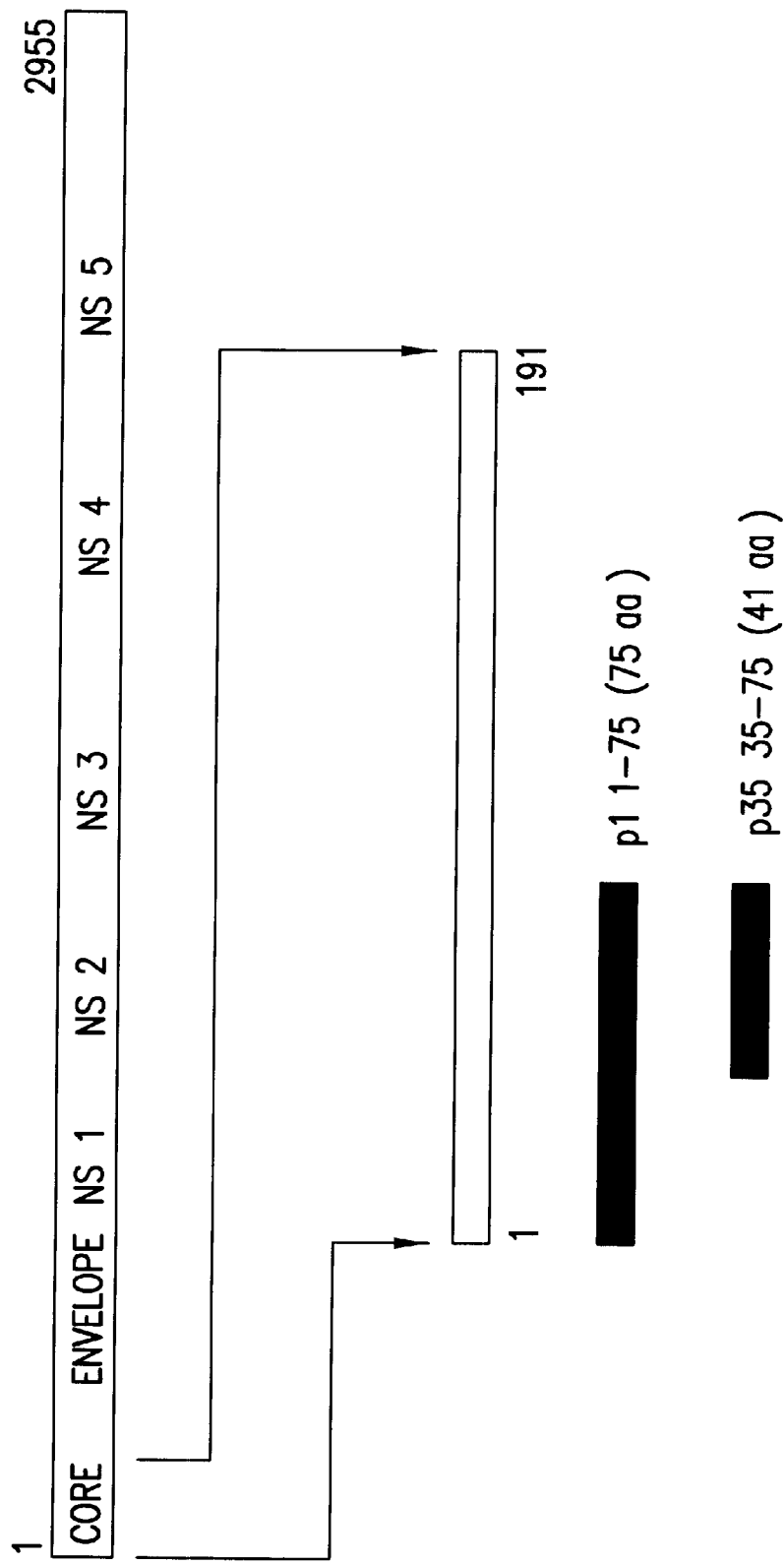
FIGS. 1a and 1b illustrate the HCV genome.
Figure 1B:
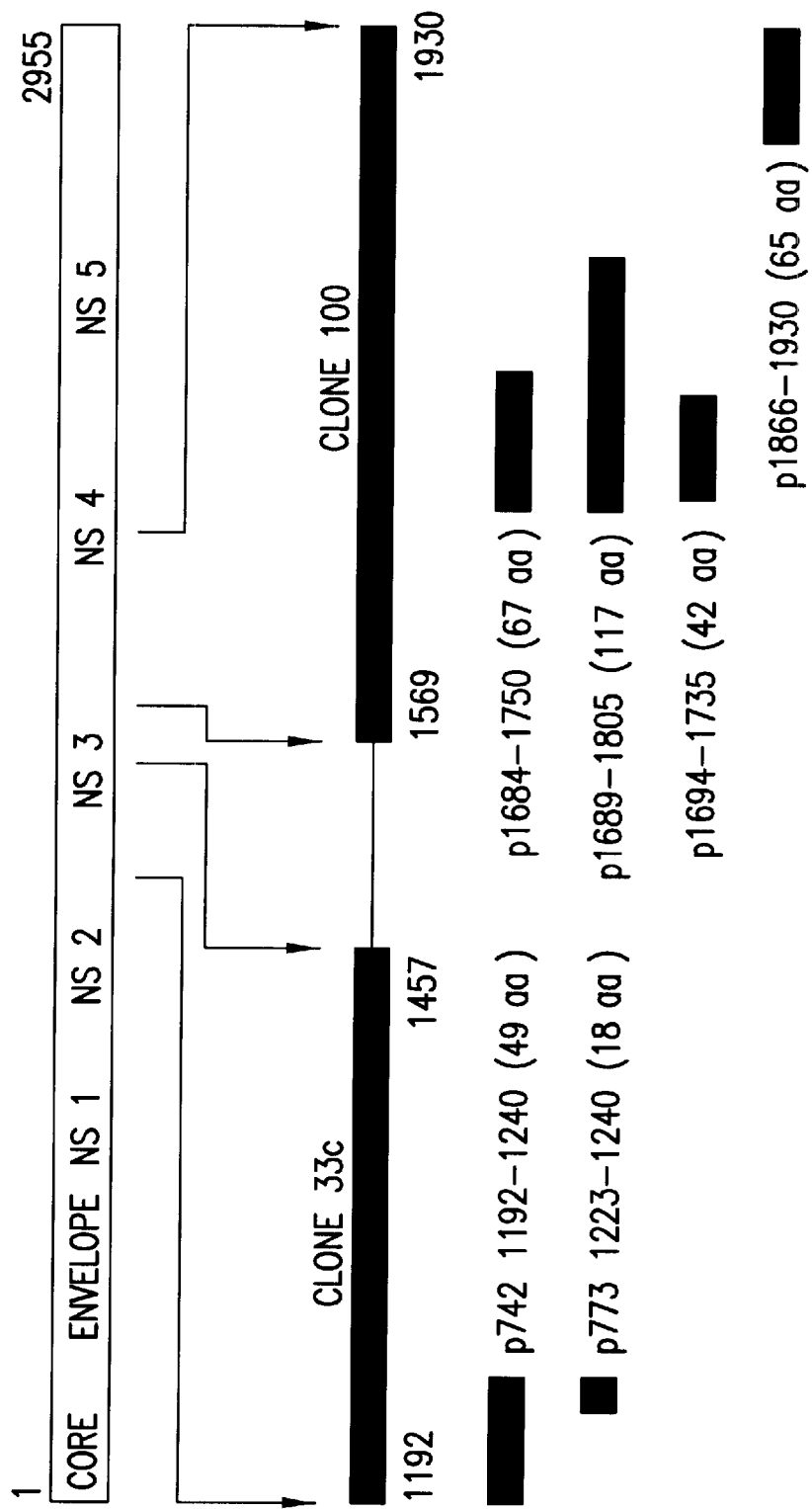
Figure 2:
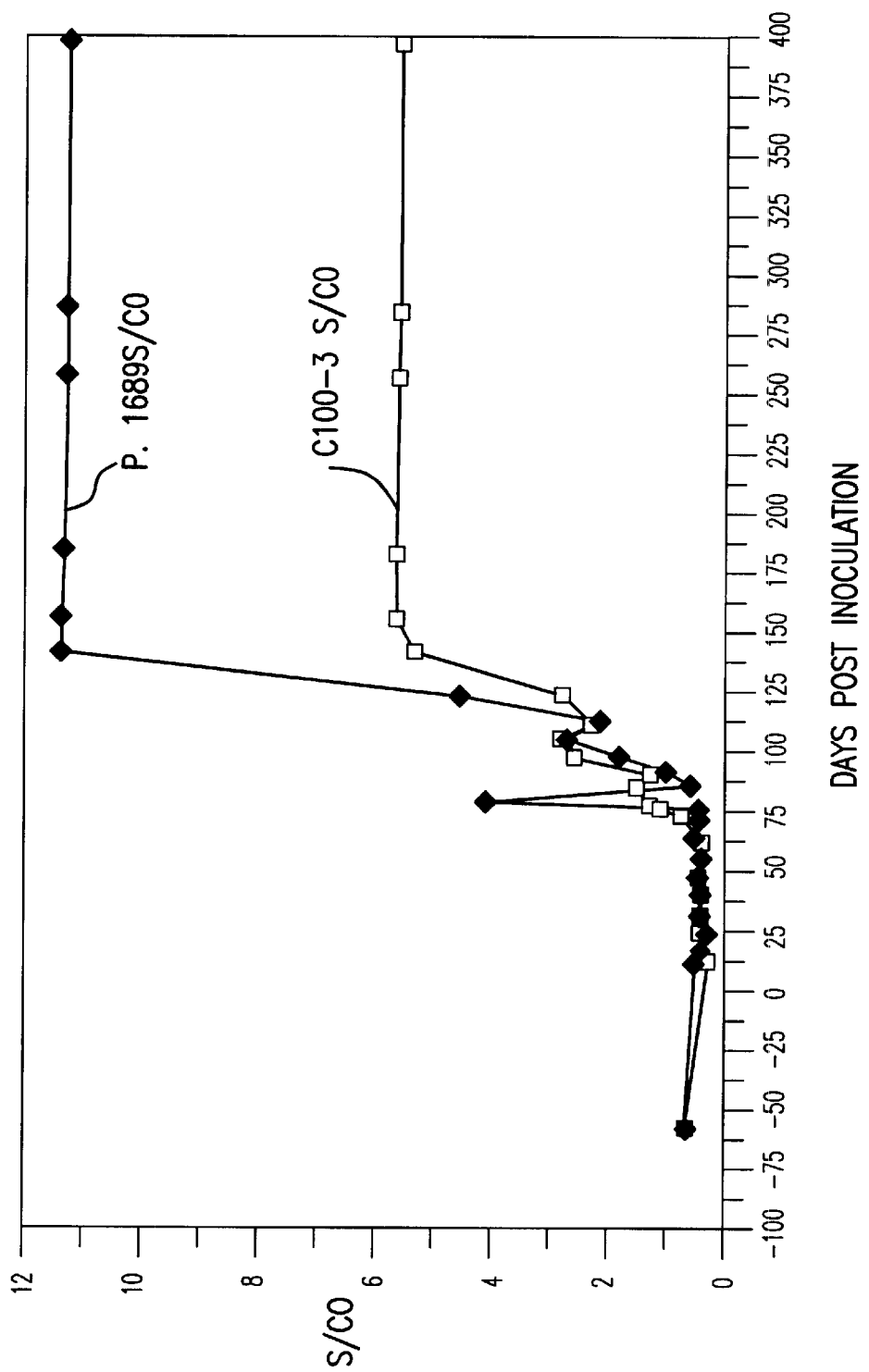
FIG. 2 illustrates the use of antigenic polypeptides to identify the presence of antibodies in a chimpanzee inoculated with HCV.

The use of polypeptides having one or more than one epitope of an HCV antigen to detect the presence of an antibody to an HCV antigen is illustrated in FIG. 2. The course of HCV infection in the chimpanzee, Melilot, was followed with one assay using recombinant C100-3 polypeptide and with another assay using p1689 polypeptide. Both assays gave negative results before inoculation and both assays detected the presence of antibodies about 100 days after the animal had been infected with HCV.

There are several known methods using both synthetic and recombinant methodologies to prepare the polypeptides of the present invention which have been found to be immunologically reactive. Preferably, the polypeptides may be prepared using automated synthesizers. The synthesis of p1684 is provided below.

Synthesis of p1684

H-GRVVLSGKPAIIPDREVLYREFDEMEECSQHIL
PYIEQGMM-
LAEQFKQKALGLLQTASRQAEVIAPAV-OH (SEQ ID NO:11)

The fully protected peptide was assembled on a phenylacetamidomethyl (PAM) resin by stepwise solid phase synthesis (starting the with carboxyl terminal residue) according to the general procedure described by G. Barany and R. B. Merrifield in *The Peptides* (E. Gross and R. Meinhoeffer, eds.) 2, 1–284 (1980) Academic Press. New York, N.Y. The C-terminal amino acid valine (Cal) was coupled to the solid support via an oxymethylphenylacetamidomethyl (OMPA) linkage to yield PAM resin which ensured improved stability to prolonged treatment with trifluoroacetic acid (TFA). A BOC-Val-OCH$_2$-PAM-resin (0.78 mmol/g, 0.13 g) was transferred to the reaction vessel of an Applied Biosystems Peptide Synthesizer, model 430A. All subsequent amino acids starting from the carboxyl terminal to N-terminus were coupled in a step-wise manner using Applied Biosystems' small scale rapid cycle protocol. Protected amino acids were coupled using preformed symmetric anhydride chemistry expect of asparagine, glutamine, arginine and histidine, which were double coupled using N-N'-dicyclohexylcarbodiimide (DCC)/1-hydroxybenzotriazole (HOBT) chemistry. In the first coupling, protected amino acids were coupled using preformed symmetric anhydrides dissolved in dimethylformamide (DMF). The symmetric anhydride of an individual amino acid was formed in methylene chloride followed by solvent exchange to DMF before transferring to the reaction vessel of the peptide synthesizer. The second coupling of symmetric anhydride was also conducted in DMF. The N-amino group of all amino acids used was protected by a t-butyloxycarbonyl (t-BOC) linkage. The side chain functional groups of various amino acids were protected by the following groups:

| | |
|---|---|
| Arg-Tos | (Tosyl) |
| Lys-2Clz | (2-Chlorobenzyloxycarbonyl) |
| Thr,Ser-Bzl | (Benzyl) |
| Tyr-2BrZ | (2-Bromobenzyloxycarbonyl) |
| Cys-4MeBzl | (4-Methylbenzyl) |
| Asp,Glu-OBzl | (O-Benzyl) |
| His-DNP | Dinitrophenyl |

The fully protected peptide-resin (0.2 g) was allowed to swell in methylene chloride (CH$_2$Cl$_2$) for five minutes. The peptide-resin was transferred to a manual reaction vessel, treated twice with 5% thiophenol in DMF for 20 minutes each followed by six CH$_2$Cl$_2$ washes for one minute each, and then transferred to the reaction vessel of the synthesizer. The t-BOC protecting group then was removed using 60% TFA/CH$_2$Cl$_2$ according to the manufacturer's protocol and the partially deprotected peptide-resin then was dried overnight under house vacuum at room temperature.

Partially deprotected peptide-resin then was treated with dimethyl sulfide (DMS [1 ml], p-cresol [1 ml], p-thiocresol [0.2 g] and HF [10 ml]) at 0° C. for one hour to cleave the peptide from the resin support. The HF/DMS and other volatiles were distilled off in vacuo at 0° C. The cleaved peptide and resin were washed three times with 15 ml aliquots of diethyl ether, and the cleaved peptide was extracted by washing three times each with 10 ml aliquots of 40% aqueous acetic acid and 15% aqueous acetic acid, respectively. The aqueous extracts were combined and washed three times with 15 ml aliquots of diethyl ether and then lyophilized to yield a crude peptide.

The crude peptide was analyzed for purity using reversed-phase high performance liquid chromatography on a C$_4$, 4.6×30 mm column (Brownlee, Applied Biosystems, Inc., Foster City, Calif.), flow rate one ml/minute employing 0.1% aqueous TFA (A) and 100% acetonitrile (B) as the solvent system. The preferred solvent gradient employed for this peptide analysis started with 30% B solvent. The column was maintained at 30% B for one minute followed by an increase over 20 minutes using a linear gradient to 55% B and maintained for one minute. Finally, the column was brought back to 30% B over a two minute period. The presence of peptide in the effluent was monitored simultaneously at 225 nm and 280 nm. The composition of the purified peptide was determined by acid hydrolysis. After removal of the acid, the hydrolysate was analyzed on a Beckmar 6300 amino acid analyzer.

If increased quantities of purified polypeptide were desired, semi-preparative reversed phase high performance liquid chromatography was performed in a similar manner using a $C_4$, 10×100 mm column (Brownlee, Applied Biosystems, Inc., Foster City, Calif.), using the same aqueous 0.1% TFA (A) and 100% acetonitrile (B) solvent system described above. The preferred solvent gradient for a semi-preparative run started with 27% B at 3 ml/minute for two minutes followed by an increase over 20 minutes using a linear gradient to 50% B. The concentration was maintained at 50% B for one minute and then reduced to 27% B within one minute.

Other peptides described herein were assembled on solid support in a manner analogous to the synthesis described above. The amino acids tryptophan and methionine, if present, were used without any side chain protection. Usually, after incorporating methionine during the chain assembly, ethanedithiol (0.1% v/v) was added to TFA for all subsequent removal of t-BOC groups. However, if histidine protected by DNP was present in the sequence, ethanedithiol was not added to TFA; instead, indole (1% v/v) was used. Also, after incorporating tryptophan, indole (1% v/v) was added to the TFA solution.

HF cleavage from the resin and purification of the peptides were achieved essentially as described above.

The peptides synthesized as described above were evaluated for their antigenic/immunogenic properties. A summary of the amino acid sequences, beginning with the amino terminus and ending with the carboxy terminus, of immunologically reactive peptides is presented in Tables 2 and 8.

TABLE 2

| | | |
|---|---|---|
| p1 (1–75) | H - M-S-T-N-P-K-P-Q-K-K-N-K-R-N-T-N-R-R-P-Q-D-V-K-F-P-G-G-G-Q-I-V-G-G-V-Y-L-L-P-R-R-G-P-R-L-G-V-R-A-T-R-K-T-S-E-R-S-Q-P-R-G-R-R-Q-P-I-P-K-A-R-R-P-E-G-R-T- OH | (SEQ ID NO:1) |
| p35 (35–75) | H-Y-L-L-P-R-R-G-P-R-L-G-V-R-A-T-R-K-T-S-E-R-S-Q-P-R-G-R-R-Q-P-I-P-K-A-R-R-P-E-G-R-T - OH | (SEQ ID NO:2) |
| p99 (99–126) | H -S-P-R-G-S-R-P-S-W-G-P-T-D-P-R-R-R-S-R-N-L-G-K-V-I-D-T-L - OH | (SEQ ID NO:3) |
| p195 (195–262) | H - R-N-S-T-G-L-Y-H-V-T-N-D-C-P-N-S-S-I-V-Y-E-A-A-D-A-I-L-H-T-P-G-C-V-P-C-V-R-E-G-N-A-S-R-C-W-V-A-M-T-P-T-V-A-T-R-D-G-K-L-P-A-T-Q-L-R-R-H-I - OH | (SEQ ID NO:4) |
| p230 (230–262) | H - V-R-E-G-N-A-S-R-C-W-V-A-M-T-P-T-V-A-T-R-D-G-K-L-P-A-T-Q-L-R-R-H-I - OH | (SEQ ID NO:5) |
| p1192 (1192–1240) | H - A-V-D-F-I-P-V-E-N-L-E-T-T-M-R-S-P-V-F-T-D-N-S-S-P-P-V-V-P-Q-S-F-Q-V-A-H-L-H-A-P-T-G-S-G-K-S-T-K-V - OH | (SEQ ID NO:6) |
| p1223 (1223–1240) | H - F-Q-V-A-H-L-H-A-P-T-G-S-G-K-S-T-K-V - OH | (SEQ ID NO:7) |
| p1357 (1357–1407) | H - Y-V-P-H-P-N-I-E-E-V-A-L-S-T-T-G-E-I-P-F-Y-G-K-A-I-P-L-E-V-I-K-G-G-R-H-L-I-F-C-H-S-K-K-K-C-D-E-L-A-A-K-L - OH | (SEQ ID NO:8) |
| p1418 (1418–1457) | H - R-G-L-D-V-S-V-I-P-T-S-G-D-V-V-V-V-A-T-D-A-L-M-T-G-Y-T-G-D-F-D-S-V-I-D-C-N-T-C - OH | (SEQ ID NO:9) |
| p1569 (1569–1593) | H - D-A-H-F-L-S-Q-T-K-Q-S-G-E-N-L-P-Y-L-V-A-Y-Q-A-T -V- OH | (SEQ ID NO:10) |
| p1684 (1684–1750) | H - G-R-V-V-L-S-G-K-P-A-I-I-P-D-R-E-V-L-Y-R-E-F-D-E-M-E-E-C-S-Q-H-L-P-Y-I-E-Q-G-M-M-L-A-E-Q-F-K-Q-K-A-L-G-L-L-Q-T-A-S-R-Q-A-E-V-I-A-P-A-V - OH | (SEQ ID NO:11) |
| p1689 (1689–1805) | H - S-G-K-P-A-I-I-P-D-R-E-V-L-Y-R-E-F-D-E-M-E-E-C-S-Q-H-L-P-Y-I-E-Q-G-M-M-L-A-E-Q-F-K-Q-K-A-L-G-L-L-Q-T-A-S-R-Q-A-E-V-I-A-P-A-V-Q-T-N-W-Q-K-L-E-T-F-W-A-K-H-M-W-N-F-I-S-G-I-Q-Y-L-A-G-L-S-T-L-P-G-N-P-A-I-A-S-L-M-A-F-T-A-A-V-T-S-P-L-T-T-S-Q - OH | (SEQ ID NO:12) |
| p1694 (1694–1735) | H - I-I-P-D-R-E-V-L-Y-R-E-F-D-E-M-E-E-C-S-Q-H-L-P-Y-I-E-Q-G-M-M-L-A-E-Q-F-K-Q-K-A-L-G-L - OH | (SEQ ID NO:13) |
| p1866 (1866–1930) | H - F-K-I-M-S-G-E-V-P-S-T-E-D-L-V-N-L-L-P-A-I-L-S-P-G-A-L-V-V-G-V-V-C-A-A-I-L-R-R-H-V-G-P-G-E-G-A-V-Q-W-M-N-R-L-I-A-F-A-S-R-G-N-H-V-S - OH | (SEQ ID NO:14) |
| p1899 (1899–1930) | H - A-A-I-L-R-R-H-V-G-P-G-E-G-A-V-Q-W-M-N-R-L-I-A-F-A-S-R-G-N-H-V-S - OH | (SEQ ID NO:15) |

Note:
H signifies the amino terminus; OH signifies the carboxyl terminus.

TABLE 8

| | | |
|---|---|---|
| p380 (380–436) | H - Gly-Val-Asp-Ala-Glu-Thr-His-Val-Thr-Gly-Gly-Ser-Ala-Gly-His-Thr-Val-Ser-Gly-Phe-Val-Ser-Leu-Leu-Ala-Pro-Gly-Ala-Lys-Gln-Asn-Val-Gln-Leu-Ile-Asn-Thr-Asn-Gly-Ser-Trp-His-Leu-Asn-Ser-Thr-Ala-Leu-Asn-Cys-Asn-Asp-Ser-Ser-Asn-Thr-Gly - OH | (SEQ ID NO:16) |
| p380.LG (380–436) | H - Gly-Val-Asp-Ala-Ala-Thr-Tyr-Thr-Thr-Gly-Gly-Ser-Val-Ala-Arg-Thr-Thr-His-Gly-Phe-Ser-Ser-Leu-Phe-Ser-Gln-Gly- | (SEQ ID NO:17) |

TABLE 8-continued

| | | |
|---|---|---|
| | Ala-Lys-Gln-Asn-Ile-Gln-Leu-Ile-Asn-Thr-Asn-Gly-Ser-Trp-<br>His-Ile-Asn-Arg-Thr-Ala-Leu-Asn-Cys-Asn-Ala-Ser-Leu-Asp-<br>Thr-Gly - OH | |
| p447<br>(447–483) | H - Phe-Asn-Ser-Ser-Gly-Cys-Pro-Glu-Arg-Leu-Ala-Ser-Cys-<br>Arg-Pro-Leu-Thr-Asp-Phe-Asp-Gln-Gly-Trp-Gly-Pro-Ile-Ser-<br>Tyr-Ala-Asn-Gly-Ser-Gly-Pro-Asp-Gln-Arg - OH | (SEQ ID NO:18) |
| p607<br>(607–627) | H - Cys-Leu-Val-Asp-Tyr-Pro-Tyr-Arg-Leu-Trp-His-Tyr-Pro-Cys<br>Thr-Ile-Asn-Tyr-Thr-Ile-Phe - OH | (SEQ ID NO:19) |
| p643a<br>(643–663) | H - Ala-Cys-Asn-Trp-Thr-Arg-Gly-Glu-Arg-Cys-Asp-Leu-Glu-<br>Asp-Arg-Asp-Ser-Glu-Leu-Ser-<u>Tyr</u> - OH | (SEQ ID NO:20) |
| p643b<br>(643–683) | H - Ala-Cys-Asn-Trp-Thr-Arg-Gly-Glu-Arg-Cys-Asp-Leu-Glu-<br>Asp-Arg-Asp-Arg-Ser-Glu-Leu-Ser-Pro-Leu-Leu-Leu-Thr-Thr-<br>Thr-Gln-Trp-Gln-Val-Leu-Pro-Cys-Ser-Phe-Thr-Thr-Leu-Pro -<br>OH | (SEQ ID NO:21) |
| p666<br>(666–683) | H - Leu-Leu-Thr-Thr-Thr-Gln-Trp-Gln-Val-Leu-Pro-Cys-Ser-<br>Phe-Thr-Thr-Leu-Pro-<u>Tyr</u>- OH | (SEQ ID NO:22) |
| p691<br>(691–714) | H - His-Leu-His-Gln-Asn-Ile-Val-Asp-Val-Gln-Tyr-Leu-Tyr-<br>Gly-Val-Gly-Ser-Ser-Ile-Ala-Ser-Trp-Ala-Ile - OH | (SEQ ID NO:23) |
| p2302<br>(2302–2352) | H - Lys-Lys-Pro-Asp-Tyr-Gln-Pro-Pro-Val-His-Gly-Cys-<br>Pro-Leu-Pro-Pro-Pro-Lys-Pro-Ser-Pro-Pro-Val-Pro-Pro-Pro-Lys-<br>Lys-Lys-Arg-Thr-Val-Val-Leu-Thr-Glu-Ser-Thr-Leu-Ser-Thr-<br>Ala-Leu-Ala-Glu-Leu-Ala-Thr-Arg-Ser-Phe - OH | (SEQ ID NO:24) |
| p380-JH1<br>(380–436) | H - Gly-Val-Asp-Gly-His-Thr-Arg-Val-Thr-Gly-Gly-Val-Gln-Gly-<br>His-Val-Thr-Ser-Thr-Leu-Thr-Ser-Leu-Phe-Arg-Pro-Gly-Ala-<br>Ser-Gln-Lys-Ile-Gln-Leu-Val-Asn-Thr-Asn-Gly-Ser-Trp-His-<br>Ile-Asn-Arg-Thr-Ala-Leu-Asn-Cys-Asn-Asp-Ser-Leu-Gln-Thr-<br>Gly- OH | (SEQ ID NO:25) |
| p380J<br>(380–436) | H - Gly-Val-Asp-Gly-His-Thr-His-Val-Thr-Gly-Gly-Arg-Val-<br>Ala-Ser-Ser-Thr-Gln-Ser-Leu-Val-Ser-Trp-Leu-Ser-Gln-Gly-<br>Pro-Ser-Gln-Lys-Ile-Gln-Leu-Val-Asn-Thr-Asn-Gly-Ser-Trp-<br>His-Ile-Asn-Arg-Thr-Ala-Leu-Asn-Cys-Asn-Asp-Ser-Leu-Gln-<br>Thr-Gly - OH | (SEQ ID NO:26) |
| p408J<br>(408–436) | H - Ser-Gln-Lys-Ile-Gln-Leu-Val-Asn-Thr-Asn-Gly-Ser-Trp-<br>His-Ile-Asn-Arg-Thr-Ala-Leu-Asn-Cys-Asn-Asp-Ser-Leu-Gln-<br>Thr-Gly- OH | (SEQ ID NO:27) |

Note:
H signifies the amino terminus; OH signifies the carboxyl terminus. The two underlined
Tyr residues are not part of the HCV sequence but are engineered there for ease of
iodinating the peptide at a later time The polypeptides illustrated in Table 2 also may be prepared in a stepwise fashion or in a fragment coupling protocol using various side chain protection methodologies known to those skilled in the art. The polypeptides also may be prepared using enzymatic methodology.

Further, the polypeptides useful in the practice of this invention may be prepared using recombinant technologies. Briefly, DNA sequences which encode the desired polypeptides are preferably assembled from fragments of the total desired sequence. The fragments are generally prepared using well known automated processes and apparatus. After the complete sequence has been prepared, the desired sequence is incorporated into an expression vector which is transformed into a host cell. The DNA sequence then is expressed by the host cell to give the desired polypeptide which is harvested from the host cell or from the medium in which the host cell is cultured. In most cases, the manufactured DNA sequence is assembled using codons which are known to be best expressed in the host cell. When smaller peptides are to be made using recombinant technologies, it may be advantageous to prepare a single DNA sequence which encodes several copies of the desired polypeptide in a connected chain. The long chain then is isolated, and the chain is cleaved into the shorter, desired sequences.

The amino acid sequence for p1684 is reverse translated to give the codons listed in Table 3 which are optimized (where not inconsistent with assembly and synthesis of fragments) to facilitate high level expression in E. coli. Individual oligonucleotides are synthesized on Applied Biosystem 380A DNA synthesizer using methods and reagents recommended by the manufacturer. These purified oligonucleotides are annealed and ligated together to assemble the entire DNA sequence for digestion with BamHI Sal, allowing ligation into pUCI8. The resulting plasmid is suitably transformed into E. coli JM103 cells. Table 3 also lists preferred codons to express p1 and p1223.

In order to establish that a clone expresses the DNA sequence, it is grown at 37° C. in 50 ml Luia Broth, in a 250 ml Ehrlenmeyer flask. When the culture reaches an OD600 of 0.3–0.5, IPGT is added to a final concentration of 1 mM to induce expression. Samples (1.5 ml) are removed at one hour intervals, and the cells are pelleted and resuspended to an OD600 of 10.0 in 2×SDS/PAGE loading buffer. Aliquots (15 $\mu$l) of the prepared samples are loaded on a 15% SDS/PAGE gel, the expressed polypeptides separated, and then electrophoretically transferred to nitrocellulose for immunoblotting. The nitrocellulose sheet containing the transferred proteins is incubated with a blocking solution for one hour and incubated overnight at 4° C. with HCV patients' sera diluted in TBS containing 5% E. coli JM103 lysate. The nitrocellulose sheet is washed three times in TBS, then incubated with HRPO-labelled goat anti-human IgG, diluted in TBS containing 10% fetal calf sera. The nitrocellulose is washed three times with TBS and the color is developed in TBS containing 2 mg/ml 4-chloro-1-napthol, 0.02% hydrogen peroxide and 17% methanol. Strong immunoreactive band formation with HCV patients' sera indicates that the synthetic polypeptide is expressed in E. coli in immunologically reactive form.

Preferred formats for assays using the polypeptides described above are provided in the following examples. However, other assay formats known to those skilled in the art can be used. These assays include ion capture assays, microparticle assays, and the use of scanning tunneling microscopy in which at least one polypeptide is attached to a solid phase, contacted with a test serum, and the surface of the solid phase is scanned for antigen-antibody complexes.

Example 1 describes a confirmatory assay. Example 2 describes a combination assay. Example 3 describes a synthetic polypeptide-based assay. Example 4 describes an immunodot assay. Example 5 describes a competition assay. Example 6 describes an EIA assay in which peptides 380–436 and 447–483, 643–683 and 2302–2352 are used. Example 7 describes an EIA utilizing peptide p380.LG. Example 8 describes an EIA utilizing peptide 2302 (NS-5) compared to an EIA utilizing antigens NS3 (CKS-33C, NS4 (C-100) or CORE (CKS-CORE). Example 9 describes the PEPSCAN protocol followed. Example 10 describes the preparation of synthetic peptides based on the sequences of four distinct HCV isolates. Example 11 describes the data obtained from studies on chronic patients and plasma donors using the peptides of Example 10. These examples are meant to illustrate, but not to limit, the scope and spirit of the present invention.

EXAMPLES

Example 1. Confirmatory Assay

The confirmatory assay uses at least two polypeptides containing HCV antigenic epitopes which are preferably prepared and isolated from different sources. One polypeptide is used to screen serum or plasma samples. The other polypeptide is used to confirm the presence of a HCV antibody in a sample initially identified as containing a HCV antibody by the screening procedure.

In the presently preferred confirmatory assay, the screening procedure uses a recombinant C100-3 polypeptide. The C100-3 recombinant polypeptide is believed to contain multiple epitopes as well an an immunodominant region defined by the 1689–1806 amino acid sequence. The C100-3 polypeptide is expressed in recombinant yeast cells and isolated from the cell extract as described in EPA Publication Number 0 318 216. Other recombinant polypeptides containing amino acid sequences essentially duplicative of C100-3 also may be used.

The other peptide used in the confirmatory assay is a synthetic peptide selected from the group consisting of p1, p35, p99, p1192, p1223, p1684, p1689, p1694, p1866, and p1899. Preferably the peptide is p1684 or p1866. These peptides were prepared following procedures described above. In the confirmatory assay, both C100-3 and the synthetic peptides, p1684, p1694 or p1866, were separately coated onto polystyrene beads. A combination of synthetic peptides coated on a polystyrene bead also may be used if desired.

The polystyrene beads are first washed with distilled water and propanol, then incubated with crude or purified HCV synthetic peptides diluted to 0.1–20.0 µg/ml in a 0.1 M solution of an appropriate buffer containing about 0.4–0.5 M NaCl, about 0.0022% Triton X-100, and adjusted to about pH 6.5–10.0. The following buffers, tris, $NaH_2PO_4 \cdot H_2O$, boric acid, and citrate buffers are preferred and are optimized for each peptide; preferred buffers, pH and coating concentration for the synthetic peptides are listed in Table 4. Successful coatings also have been accomplished with lower or higher pH. The beads are incubated in the antigen solution for about two hours at 38–42° C., washed in phosphate buffer solution (PBS) and soaked in 0.1% Triton X-100 in PBS for 60 minutes at 38–42° C. The beads then are washed two times in PBS, overcoated with a solution of 5% (w/v) bovine serum albumin (BSA) in PBS for 60 minutes, and washed three times with PBS. Finally, the beads are overcoated with 5% (w/v) sucrose in PBS and dried under nitrogen or air.

The peptides are each individually coated onto polystyrene beads and used in an antibody capture format. Ten microliters of sample are added to the wells of a reaction tray along with 400 µl of a sample diluent and a peptide coated bead. The sample diluent consists of about 10% (v/v), or less, bovine serum and about 20% (v/v), or less, goat serum in 20 mM Tris phosphate buffer containing 0.20%, or less, (v/v) Triton X-100, 3% (w/v), or less, BSA. When the recombinant yeast C100-3 polypeptide is used, antibodies to yeast antigens which may be present in a test sample are reacted with yeast extracts which are added to the sample diluent (typically about 200 µg/ml). The addition of yeast extracts to the sample diluent is used to prevent false positive results. The final material is sterile filtered and filled in plastic bottles, and preserved with 0.1% sodium azide.

After one hour of incubation at 40° C., the beads are washed and 200 µl of conjugate is added to the wells of the reaction tray.

The preferred conjugate is goat anti-human IgG horseradish peroxidase conjugate. Concentrated conjugate is purchased from Kirkegaard and Perry Laboratories, Inc., Gaithersburg, Md., and is titered to determine a working concentration. A 20-fold concentrate of the working conjugate solution is then prepared by diluting the concentrate in diluent. The conjugate diluent includes 10% (v/v) bovine serum, 10% (v/v) goat serum and 0.15% Triton X-100 in 20 mM Tris buffer, pH 7.5 with 0.01% gentamicin sulfate, pink dye and antifungal agents as preservatives. The conjugate is sterile filtered and filled in plastic bottles.

After one hour of incubation with the conjugate at 40° C., the beads are washed, exposed to the OPD substrate for 30 minutes at room temperature, and the reaction terminated by the addition of 1 N $H_2SO_4$. The absorbance is read at 492 nm.

Samples found to be repeatably reactive by a screening assay using the polypeptide C100-3 are tested in duplicate using p1684 or p1689 coated beads. Reactive specimens are considered confirmed samples. Samples not reacting with p1684 or p1689 are tested in duplicate with p1694 and p1866 beads. Samples reacting with one or both of these peptides are considered confirmed. Those specimens not reacting with any of these peptides are considered nonconfirmed.

In order to maintain acceptable specificity, the cutoff for the assay should be at least 5–15 standard deviations above the absorbance value of the normal population mean. Consistent with these criteria, a cutoff for the assay may be selected which clearly separated most of the presumed "true negatives" from "true positive" specimens. A general cutoff value may be calculated as about 2.1 to 8 times the negative control mean absorbance value.

Confirmatory Assay Performance

1. Intravenous Drug User Samples

Samples were collected from a population of intraveneous drug users enrolled in an NIH-funded study. The population consisted of individuals who were acknowledged users of intraveneous drugs selected over a two-year period from patients at the Edward Hines Jr. Veteran's Administration Hospital in Maywood. Ill. by Dr. Connie Pachucki and members of the Infectious Diseases staff.

As illustrated in Table 5, a total of 296 specimens, each obtained from a single donor, were screened using recombinant yeast C100-3 polypeptide. A total of 271 of 296 (91.6%) specimens initially tested positive; upon retesting, 269 of 271 (99.3%) were repeat-positives.

Confirmatory testing indicated that 263 of 269 (97.8%) of the repeat positives were reactive with p1689, five specimens were non-reactive with p1689, and one specimen was not tested with any of the confirmatory polypeptides. Four of the five specimens which were non-reactive with p1689 were reactive with p1866 only; one specimen which was non-reactive with p1689 was reactive with only p1694.

All specimens which were repeatably reactive were confirmed reactive in assays using the HCV synthetic peptides.

TABLE 5

INTRAVENEOUS DRUG USERS SAMPLES

| C100-3 Initial Pos. | C100-3 Repeat Pos. | p1689 | p1866 | p1694 | No. of Repeat Positives Confirmed |
|---|---|---|---|---|---|
| 271/296 | 269/271 | 263/269 | 4/5 | 1/5 | 268/269 |

2. Chimpanzees Samples

Confirmatory assays were used to evaluate 92 samples from six chimpanzees. All were initially reactive with recombinant C100-3. (Duplicative, repeat testing of chimp sera was not done because of the rare nature of these specimens and their utility for serological studies with other HCV antigens). Eighty-three of 92 (90.2%) specimens were confirmed reactive using p1689. Confirmation of initial reactives improved to 96.7% (89 of 92) when repeat testing with p1694 and p1866 was done.

3. Chiron Corporation Non-A, Non-B Hepatitis Virus Proficiency Panel #2

A proficiency panel comprised of neat and diluted human plasma including specimens containing antibodies to HCV C100-3 was provided by scientists at the Chiron Corporation (12 specimens). This panel contains specimens ranging from low to high reactivity in other assays, non-reactive presumed "true negative" specimens, and reactive specimens diluted to give low-level or negative results.

Results using the confirmatory assay on the Chiron Corporation Non-A, Non-B Hepatitis Virus Proficiency Panel #2 indicated 9 of 9 (100%) of the specimens reactive by the preliminary screening assay are confirmed by p1689. All negative specimens were non-reactive.

4. Confirmatory Testing on NANB Panel II

A panel of highly pedigreed human sera from Dr. H. Alter, NIH, Bethesda, Md., containing infectious HCV sera, negative sera and other disease controls were tested. A total of 44 specimens were present in the panel.

All specimens (16/16, 100%) reactive in the assay using C100-3 were confirmed by p1689, as shown in Table 6. Again, there were no nonspecific reactives as all pedigreed negative or "other disease" controls were non-reactive in the peptide assay.

Data presented demonstrate the efficacy of the confirmatory assay for detection of antibodies to HCV antigens. The current assay is both sensitive and specific for detection of antibodies to HCV antigens.

The data further support the utility of the confirmatory strategy using synthetic peptides. The synthetic peptides serve as an independent source of antigen for use in immunoassays. The ability to confirm an average of 99% of repeatably reactive specimens in high risk or pedigreed positive HCV panels, establishes the utility of this strategy.

Example 2. Combination Assay

The combination assay uses more than one polypeptide antigen coated on the same bead. To prepare multiple polypeptide-containing beads, the polystyrene beads described in Example 1 are contacted simultaneously with the polypeptide in appropriate buffer solutions. After the beads have been contacted with the polypeptides, the bead is treated further as described above.

Figure 3A:
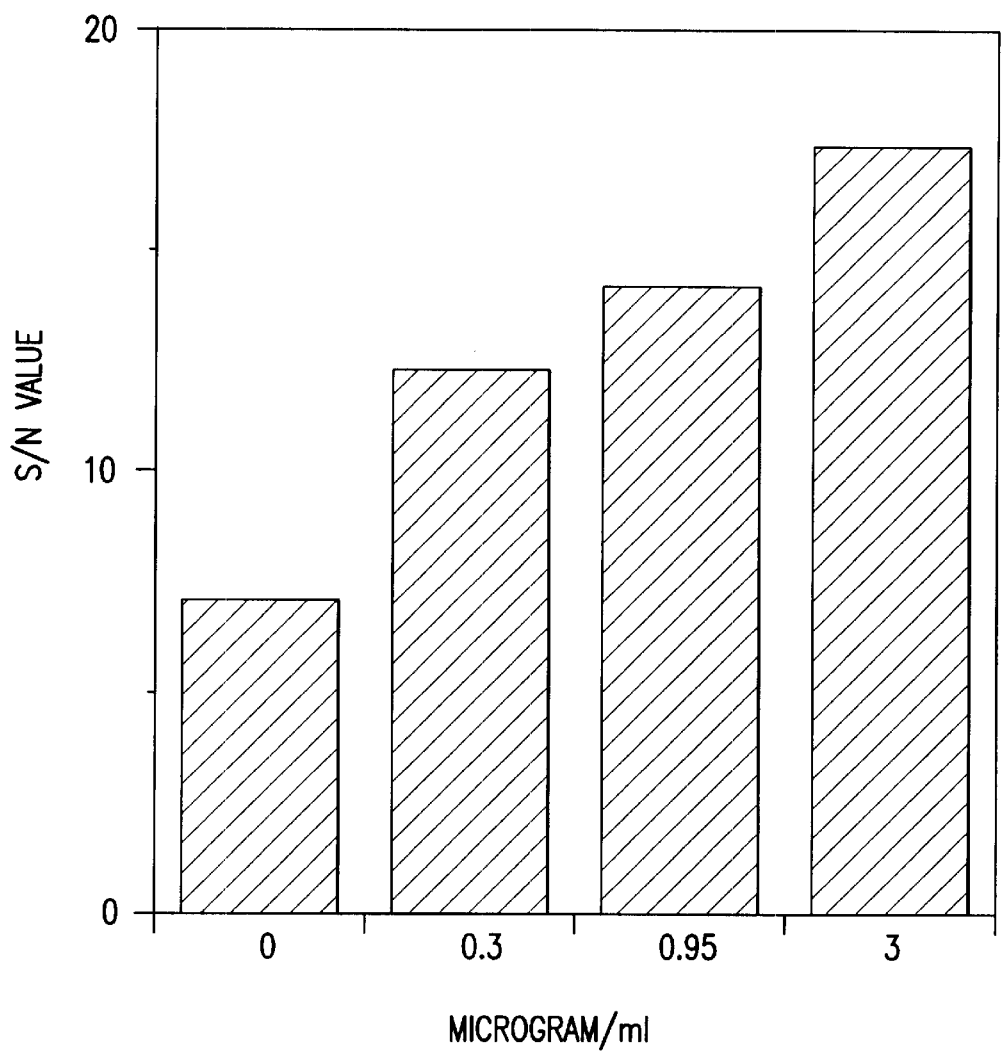
FIGS. 3a and 3b illustrate the sensitivity increase using a combination assay format.
Figure 3B:
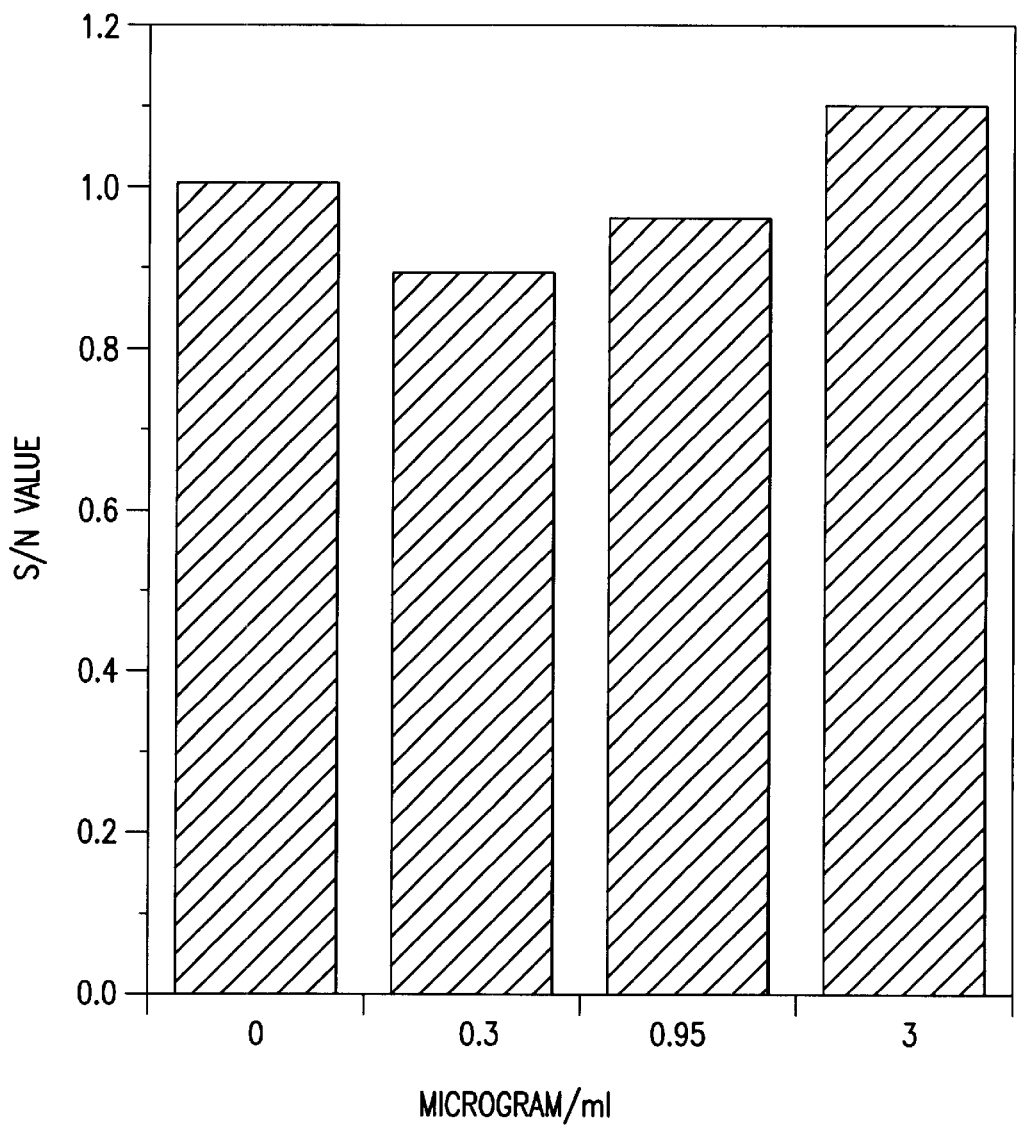

For a polystyrene bead containing both C100-3 and p1694, the sensitivity of the assay increases. As graphically illustrated in FIG. 3a, adding about 0.3, 0.95, and 3 micrograms of p1694 to the coating solution, respectively, shows a significant increase in the signal when the detection procedures of Example 1 are utilized. FIG. 3b graphically illustrates the data which show no corresponding increase in the signals (such as may attend non-specific binding) generated from negative human plasma.

Example 3. Synthetic Polypeptide-based Assay

The use of synthetic polypeptides which contain epitopes of HCV antigens provide immunological assays which have increased sensitivity and may be more specific than HCV immunological assays using the SOD fusion polypeptide C100-3. The use of shorter amino acid sequences on polystyrene beads provides an increase in sensitivity.

The increased sensitivity of an assay employing synthetic polypeptide compared to recombinant C100-3 polypeptide was demonstrated in a serial dilution study. The serial dilution study employed 15 samples which were identified as having antibodies to HCV antigens using a recombinant C100-3 screening assay. Each positive sample was assayed using recombinant C100-3 polypeptide in one assay and p1689 polypeptide in a second assay, and the samples were then diluted twofold until the S/CO value was less than one. In 12 samples, the p1689 polypeptide gave increased sensitivity (larger S/CO values) at all dilutions. In two samples, the p1689 polypeptide and the recombinant yeast C100-3 polypeptides were essentially equivalent. In one sample, the p1689 polypeptide have a negative response to a positive sample at all dilutions.

Additional studies on samples from serial bleeds of three chimps which developed an acute resolved case of HCV infections and three chimps which developed chronic HCV infections showed different immunological responses believed to be due to both the type of infection and the polypeptide used in the assay. This study assayed serum from serial bleeds of six chimps inoculated with HCV. The assay protocols were similar to those described in Example 1 above with the following differences.

The antibodies, IgG, IgM, and IgA were detected using affinity purified goat antibodies to human IgG, IgM and IgA coupled to horseradish peroxidase (Kirkegaard & Perry Laboratories, Inc., Gaithersburg, Md.) which were used at working concentrations of 0.2 µg/ml anti-IgG, 0.5 µg/ml anti-IgM and 0.2 µg/ml anti-IgA. Serum dilutions for each assay were 1:41 for IgG, 1:101 for IgM and 1:41 for IgA.

The polypeptides that were used in the study include C100-3, p1694, p1689 and p1866.

Briefly, beads containing the polypeptides were incubated with diluted serum for one hour at 40° C., the beads then were washed and incubated with the appropriate goat antibody for one hour at 40° C. The beads were washed again and the assay was developed by incubating the beads with OPD for 30 minutes at room temperature. The color development was quenched with 1 N sulfuric acid and the results read at 492 nm.

All chimps developed antibodies that were detected by C100-3, p1684, and p1866 within seven to 17 wells post-inoculation (WPI). Within each chimp, IgG antibody reacting with C100-3, p1684, and p1866 appeared at approximately the same time. The response to p1694 and p1866 was variable within that time period with indications that antibody to these two peptides can be either undetectable or significantly delayed following HCV infection. These data suggest that, out of the five peptides tested, antibody to C100-3, p1684, or p1689 would be the earliest and most consistent serologic indicator of HCV infection.

IgM antibody was detected in only three of the six chimps studied. The response of each of the three animals to C100-3, p1684, p1689 and p1694 was detected in seven to ten WPI whereas IgM antibody to p1866 was undetectable in two chimps and delayed in the third. All IgM responses were short lived with levels falling below positive (S/N less than 3.0) within two to 22 weeks.

The explanation and significance of finding IgM antibodies in three chimps with acute resolved disease while not detecting IgM antibodies in three chimps with chronic infection is unexpected. Preliminary experimental results indicated that false negative IgM results due to preferential IgM binding is an unlikely explanation. If the pattern observed in these six chimps with the five peptides holds true, antibody assays will provide important HCV prognostic information.

A positive IgA response (S/N greater than 3.0) was detected in only two of the six chimps, and proved to be either biphasic or significantly later than the IgG or IgM response. Although these two chimps had chronic disease, no conclusions regarding the significance of IgA antibodies can be made since sera from the three resolved chimps is available only through 30 to 40 WPI.

The results show the polypeptides when used to assay for antibodies to HCV antigens are useful to follow the progression of HCV infection, and that the polypeptides exhibit unexpected sensitivity to different antibodies generated during the clinical progression of HCV infection.

Example 4. Immunodot Assay

Figure 4:
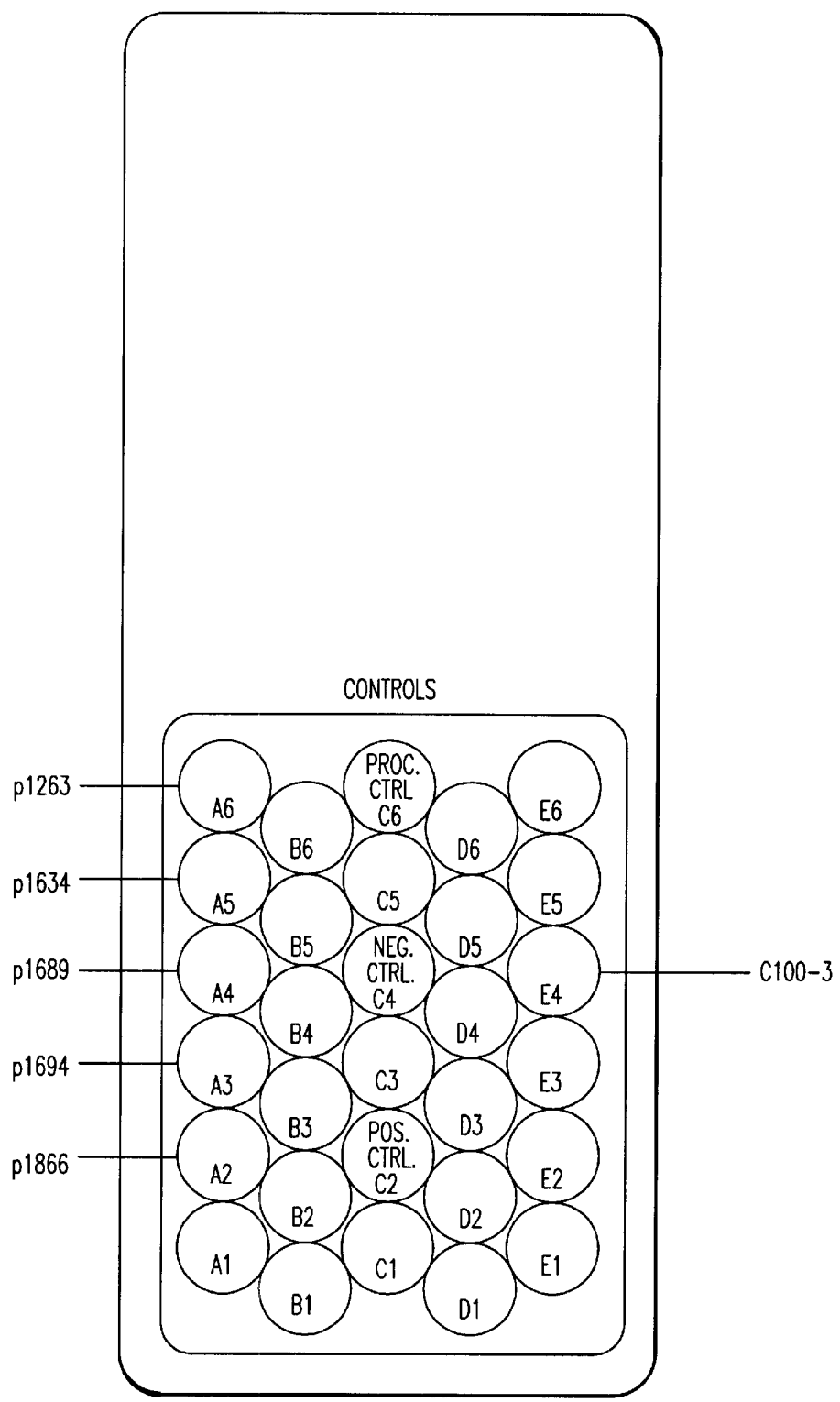
FIG. 4 illustrates a test cartridge for an immunodot assay.

The immunodot assay system uses a panel of purified synthetic polypeptides placed in an array on a nitrocellulose solid support. The prepared solid support is contacted with a sample, and captures specific antibodies to HCV antigens. The captured antibodies are detected by a conjugate-specific reaction. Preferably, the conjugate-specific reaction is quantified using a reflectance optics assembly within an instrument which has been described in U.S. patent application Ser. No. 07/227,408, filed Aug. 2, 1988. The related U.S. patent applications Ser. Nos. 07/227,272, 07/227,586 and 07/227,590 further describe specific methods and apparatus useful to perform an immunodot assay. Briefly, a nitrocellulose-base test cartridge which may be used in an automated process for performing an immunodot assay described above is illustrated in FIG. 4. Each polypeptide is contained within a specific reaction zone on the test cartridge. After all the antigenic polypeptides have been placed on the nitrocellulose, excess binding sites on the nitrocellulose are blocked. The test cartridge then is contacted with a test sample such that each antigenic polypeptide in each reaction zone will react if the sample contains the appropriate antibody. After reaction, the test cartridge is washed and any antigen-antibody reactions are identified using suitable well-known reagents.

As described in the patent applications listed above, the entire process is amenable to automation. The specifications of these applications related to the methods and apparatus for performing an immunodot assay, listed above, are incorporated herein by reference.

In a preferred immunodot assay, the synthetic polypeptides p1223, p1684, p1689 and p1866 were diluted into an aqueous buffered solution (polypeptide diluent: 0.03% Triton X-100 and 0.1% sodium azide in 50 mM Hepes buffer, pH 7.6) and applied to a preassembled nitrocellulose test cartridge at about 40 ng in each reaction zone. After drying the cartridge overnight at room temperature, the nonspecific binding capacity of the nitrocellulose phase was blocked. The blocking solution contained 1% porcine gelatin, 1% casein enzymatic hydrolysate, 5% Tween-20, 0.1% sodium azide, 0.5 M sodium chloride and 20 mM Tris, pH 7.5.

Test cartridges were incubated with samples 00642 and 423 (see Table 1) and ALT 27. The sample ALT 27 was obtained from a volunteer donor having elevated alanine aminotransferase levels. After sample incubation, sequential incubations with a biotin-conjugated goat anti-human immunoglobulin-specific antibody, an alkaline phosphatase-conjugated rabbit anti-biotin specific antibody, and 5-bromo-4-chloro-3-indolyl phosphate produced a colored product at the site of the reaction.

A detectable reaction is defined by the formation of a visually discernable product at the antigen site on the array; when quantified by the instrument, a reflectance density (Dr) value of greater than or equal to approximately 0.0150 above background is obtained. None of the tested polypeptides elicited a detectable reaction with a negative control serum that was previously demonstrated negative for antibodies to HCV antigens using a recombinant C100-3 polypeptide.

A reaction with each of the synthetic polypeptides p1684, p1689, p1694 and p1866 occurred when the prepared test cells were incubated with either sample 00642 (1:100 dilution in negative serum) or sample 423 (1:40 dilution in negative serum). Polypeptide p1223, in addition to polypeptides p1684, p1689, p1694 and p1866 demonstrated a significant reaction with the elevated ALT 27 specimen. In all specimens, highest reactivity was obtained with p1689. Enhanced reactivity of polypeptide p1684 with sample 00642 was achieved through subtle modification of the antigen dilution (the modified polypeptide diluent was 0.5 M sodium chloride, 0.0022% Triton X-100 and 0.1 M Tris/HCl, pH 8.5).

The net reflectance (Dr) for a test cartridge containing the polypeptides p1223, p1684, p1689, p1694 and p1866 which indicate a positive or negative response is set out in Table 7.

Example 5. Competition Assay

The synthetic peptides containing antigenic HCV epitopes are useful for competition assays. To perform a neutralization assay, peptides representing epitopes within the C100-3 region such as p1694, p1684 or p1689 are 34 and mixed with a specimen diluent to a final concentration of 0.5–50 $\mu$g/ml. Ten microliters ($\mu$l) of specimen or diluted specimen is added to a reaction well, followed by 400 $\mu$l of the specimen diluent containing peptide and if desired, the mixture may be pre-incubated for about 15 minutes to two hours. A bead coated with C100-3 antigen of HCV then is added to the reaction well and incubated for one hour at 40° C. After washing, 200 $\mu$l of peroxidase labeled goat anti-human IgG in conjugate diluent is added and incubated for one hour at 40° C. After washing, OPD substrate is added and incubated at room temperature for 30 minutes. The reaction is terminated by the addition of 1 N sulfuric acid, and the absorbance read at 492 nm.

Samples containing antibodies to the C100-3 antigen generate a reduced signal caused by the competitive binding of the peptides to these antibodies in solution. The percentage of competitive binding may be calculated by comparing the absorbance value of the sample in the presence of a synthetic peptide to the absorbance value of the sample assayed in the absence of a synthetic peptide at the same dilution.

Example 6. EIA Assay

Beads were coated with either peptides 380–436 and 447–483, 643–686 or 2302–2353 according to the method described in Example 1, except that peptides 380–436 and 447–483 were coated simultaneously on the same solid phase, both sequences being from the putative envelope region of HCV. Either peptide alone had activity in this type of assay. EIA was performed using each bead configuration described herein. The EIA method performed was as is described in Example 1, with the cutoff set at four times the negative control value. Table 9 presents data obtained from these assays in which serum specimens from patients diagnosed with chronic NANBH were assayed.

TABLE 9

| ANTIGEN # POS./NO. TESTED | | |
|---|---|---|
| p380 | p643b | p2302 |
| 70/165 (42%) | 62/165 (38%) | 102/165 (62%) |

Example 7. EIA Utilizing p380.LG and p380

Beads were coated with either p380.LG or p380 according to Example 1. An EIA following the procedures of Example 1 was used to assay samples. As can be seen by the data presented in Table 10, the p380.LG peptide detected antibody in specimens that were negative to p380. The HCV sequence is highly variable in the region 380–436 a.a. Therefore, there is reasonable probability that differentiation between HCV "serotypes" based on reactivity of human specimens to one or the other of these envelope region peptide sequences is possible. The data of Table 10 suggest that p380.LG can detect chronically infected HCV patients who are negative to p380.

TABLE 10

| | p380 | | p380.LG | |
|---|---|---|---|---|
| SAMPLE | OD | S/N | OD | S/N |
| #8 | .155 | 2.12 | .399 | 5.87 |
| #28 | .246 | 3.37 | .950 | 13.97 |
| #23 | .114 | 1.56 | .458 | 6.74 |

Example 8. EIA Utilizing p2302

Figure 5:
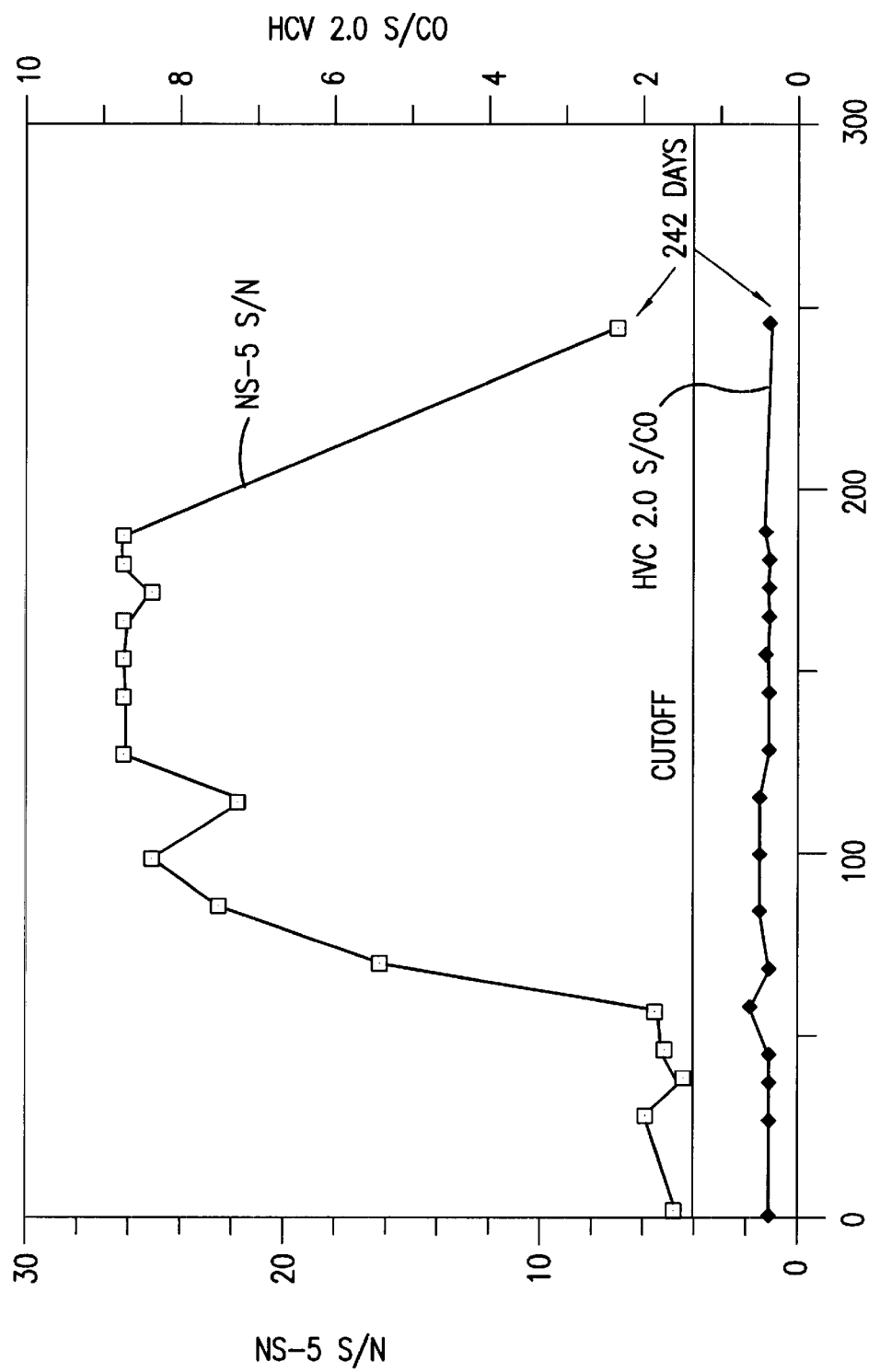
FIG. 5 illustrates a seroconversion graph wherein the amount of anti-NS5 S/N antibody, shown as the solid line between closed circles, and the amount of anti-HCV 2.0 S/CO antibody shown as a solid line between open squares, is plotted against days post presentation.

Beads were coated with either p2302 or recombinant HCV antigens according to the method of Example 1. The bead coated with recombinant antigens comprised antigens from the NS3 (CKS-33C), NS4 (C-100) and Core (CKS-CORE) regions of the HCV genome. A patient sample which exhibited seroconversion to p2302, but not to antigens of HCV 2.0, is shown in FIG. 5. Thus, this peptide improves the ability to detect HCV infected individuals.

Example 9. Pepscan Protocol

NS1 region of HCV genome from a.a. 600–720 was mapped with PEPSCAN analysis, which is serological analysis of series of overlapping peptides spanning the protein sequence to identify immunogenic domains. A total of 106 overlapping hexamer peptides were synthesized on polypropylene pins following the manufacturer's instructions (Cambridge Research Bioscience, Valley Stream, N.Y.). Fab dimers of IgG purified from sera of individuals seropositive for HCV were tested with these peptides. Based on the reactivity in EIA (performed as described by the manufacturer) four peptide sequences were selected as illustrated in Table 11.

Each of these peptides were synthesized by a stepwise solid phase synthesis, starting the the carboxy terminus residue. A panel of sera positive for antibodies to C-100 protein of HCV was tested for their reactivity to NS peptide by microtiter EIA as described below.

EIA PROTOCOL

Wells of microtiter plates were coated with 100 µl of the peptide at 10 µg/ml in 0.02 M bicarbonate buffer, pH 9.5 at ambient temperatures for 12–16 hours. After washing with phosphate buffered saline (PBS) which also contained 0.01% sodium dodecyl sulfate (SDS) and 0.05% Tween-20® (available from BioRad Laboratories, Richmond, Calif.), free sites were overcoated with 1% BSA in bicarbonate buffer pH 9.5. Plates were stored at 4° C. following a final wash.

Sera from individuals seropositive for antibodies to HCV C-100 were serially diluted in 100 µl of a buffer containing 20 mM sodium phosphate, pH 7.4, 0.15 M NaCl, 20% normal goat serum, 10% fetal calf serum, 5 mM EDTA, 10 mM EGTA, 50 mM Tris, 0.2% Tween-20 with sodium azide as preservative, pH 6.8. The diluted sera were reacted with peptides in microtiter wells for three hours at 37° C. or overnight at ambient temperatures. The plates were washed and 100 µl of appropriately diluted goat anti-mouse (HH) Horseradish Peroxidase (HRPO)-conjugated antibody (Jackson Immunochemicals, West Grove, Pa.) was added. The plates were incubated at 37° C. for two hours. After a final wash, 100 µl of O-phenylenediamine 2HCl (OPD) color regent was added. The reaction was carried out at room temperature in the dark for 20–25 minutes, and stopped by the addition of 100 µl of 1N $H_2SO_4$. The absorbance of the reaction mixture was recorded at 492 nm. A negative control which was previously confirmed to be negative for HCV infection was included with each plate in triplicate. The sample was considered reactive if the absorbance of the sample at a 1:2000 dilution was three times the absorbance of the negative control at the same dilution. Table 12 illustrates the reactivity of these samples with each of the peptides.

The legend for Table 12 is as follows:
+ =Sample showing A492 3xnegative control
++=Sample titering to 1:5000 dilution
+++=Strong reactivity with sample titering to 1:10,000 dilution.

Example 10. Synthetic Peptides to 5' End of E2/NS1

The 5' end of the E2/NS1 putative structural region of HCV has been shown to be hypervariable with respect to both nucleic acid and amino acid content among multiple virus isolates studied throughout the world. It has been speculated but not proven, that this region is involved in a viral mechanism to defeat host immune surveillance. If this region were to mutate under humoral immune selective pressures, then specific antibody responses to genotypic variants of the virus should be detectable in HCV infected patients. We demonstrated the presence of multiple epitopes within this hypervariable region, thus supporting the hypothesis that, as in flaviviruses and pestiviruses, this E2/NS1 region is exposed to the host's immune system and the subsequent selective pressures toward antigenically distinct variants.

Synthetic peptides were prepared based on the sequences of four distinct HCV isolates. The peptides represented the sequence from amino acid 380 through amino acid 436 of the large open reading frame of HCV. A smaller peptide encoded by amino acids 408–436 also was synthesized. The sequences were obtained from HCV-1 (Chiron prototype), HCV G83 (p380.LG), HCV-JH-1 and HCV-J. Peptide HCV-JH-1 was as described by K. Takeuchi et al., *Nucleic Acids Research* 18:46226 (1989), while peptide HCV-J was as described by N. Kato et al., *Proc. Nat'l. Acad. Sci.* 87:9524–9528 (December, 1990). Though encoded by the same genomic region, each of these peptides are divergent from each other by a minimum of 25% (range 25–35%) based on amino acid sequence over the span of 57 amino acids. Peptide 408–436 was prepared based on the sequence of HCV-JH-1 and HCV-J which are identical in this region. Each of these peptides was coated onto a solid phase under the coating conditions listed in Table 4 and used as antigenic targets in separate enzyme immunoassays (EIAs), according to the methods described hereinabove for EIA. The specificity of the individual EIA's were demonstrated by testing populations of normal plasma donors. A cutoff value of 4 times the negative control sample was used for all analyses. Populations of chronic HCV patients from the U.S. and Italy, acute phase HCV patients from the U.S. and Italy, and HCV antibody positive plasma donors from the U.S. and Japan were tested.

Data from studies on chronic patients and plasma donors is presented in Table 13. Antibodies were detected to each of the four distinct synthetic peptides in chronic HCV patients. The most commonly recognized serotype among U.S. patients was HCV-1 (43.5%), while the least reactive was HCV-J (12.9%). However, among Italian patients, the HCV-G83 was the most prevalent serotype (52.0%), and HCV-1 (12.0%) was least commonly seen in these patients. The most commonly recognized HCV variant in U.S. plasma donors positive for other HCV antibodies was HCV-1. Conversely, the HCV-1 variant was the least recognized variant among Japanese donors. The HCV-G83 variant was recognized most frequently in Japanese donors, and was nearly as reactive as HCV-1 in the U.S. donors as well.

Seroconversion to at least one of these serotypes has been observed in the acute phase of several HCV infected patients. Loss of antibody signal to one serotype and the concurrent seroconversion to a second serotype has been observed in one patient.

Among the group of U.S. plasma donors were three specimens which had detectable antibody to all four variant peptides used, suggesting the presence of at least one conserved epitope within the 380–436 region. Since the sequences within the second half (a.a. 408–436) of this region are more conserved among the four virus isolates, this peptide was prepared based on the HCV-JH-1 and HCV-J sequences which are identical in this region. All three of these specimens were also reactive to this smaller, more conserved region, which demonstrated the existence of a conserved epitope within these boundaries.

TABLE 13

HCV SEROTYPE ANALYSIS

| Population | Reactivity to Peptide From Isolate: | | | | |
|---|---|---|---|---|---|
| | HCV-1 | G83 | JH-1 | J | TOTAL |
| US Chronics | 29/62 | 20/62 | 17/62 | 8/62 | 36/62 |
| N = 62 | (43.5%) | (32.3%) | (27.4%) | (12.9 | (58.1%) |
| Unique Reactives | 1/36 | 3/36 | 4/36 | 0/36 | 8/36 |
| | (2.8%) | (8.3%) | (11.1%) | | (22.2%) |
| Italy Chronics | 6/50 | 26/50 | 19/50 | 8/47* | 34/60 |
| N = 50 | (12.0%) | (52.0%) | (38.0%) | (17.0%) | (68.0%) |
| Unique Reactives | 1/34 | 11/34 | 6/34 | 1/30* | 19/34 |
| | (2.9%) | (32.4%) | (17.7%) | (3.3%) | (58.8%) |
| U.S. HCV Positive | | | | | |
| Plasma Donors | 16/55 | 12/55 | 10/55 | 5/48* | 22/55 |
| N = 55 | (29.1%) | (21.8%) | (18.2%) | (10.4%) | (40.0%) |
| Unique Reactives | 6/22 | 5/22 | 1/22 | 0/17* | 12/22 |
| | (27.3%) | (22.7%) | (4.6%) | | (54.6%) |
| Japan HCV Positive | | | | | |
| Plasma Donors | 1/27 | 13/27 | 9/27 | 4/27 | 18/27 |
| N = 27 | (3.7%) | (48.2%) | (33.3%) | (14.8%) | (68.7%) |
| Unique Reactants | 0/18 | 5/18 | 2/18 | 3/18 | 10/18 |
| | | (27.6%) | (11.1%) | (16.7%) | (55.6%) |

*Some samples depleted.

Our data thus demonstrates the existence of at least two epitopes within the hypervariable region of HCV E2/NS1. We conclude that genotypic variability in this region resulted in antigenically distinct HCV variants. Unique E2/NS1 antibody responses can be found in patients with acute and chronic phase HCV infections, as well as in plasma donors from different parts of the world. Our preliminary data thus points to the possibility of geographic variability with regard to antibody responses to HCV as well. It is likely that a high proportion of patients with chronic HCV infection have antibody to the hypervariable region of E2/NS1, since we detected 58% and 68% of U.S. and Italian chronic patients, respectively, as reactive to this region using sequences from only four HCV isolates. The implications for HCV vaccine development are significant if virus neutralizing epitopes exist within this hypervariable region.

It is envisioned that these peptides may be used for the development of unique polyclonal and monoclonal antibodies. The polypeptides of this invention, along with those described in U.S. patent application Ser. Nos. 07/456,162 and 07/610,180 (both of which were previously incorporated herein by reference) can be used in combination to develop unique assays for the detection of various epitopes of HCV. This combination of polypeptides can be accomplished, for example, by coating a solid surface with more than one peptide, or by utilizing a mixture of solid supports, wherein the mixture comprises a unique blend of two or more polypeptides to HCV. These techniques are known to the routineer. Other variations of applications and modifications of the specific embodiments of the invention as set forth herein will be apparent to those skilled in the art. Accordingly, the invention is intended to be limited only in accordance with the appended claims.

TABLE 4

| PEPTIDE | COATING CONC. μg/ml | COATING BUFFER | OTHER COMPONENTS IN COATING SOLUTION |
|---|---|---|---|
| 1–75 | 2.0 | 0.1M NaPhosphate, pH 6.5 | 0.4M NaCl, .0022% Triton X-100 |
| 35–75 | 2.0 | 0.1M NaPhosphate, pH 6.5 | 0.4M NaCl, .0022% Triton X-100 |
| 99–126 | 2.0 | 0.1M NaPhosphate, pH 6.5 | 0.4M NaCl, .0022% Triton X-100 |
| 195–262 | 2.0 | 0.1M NaPhosphate, pH 6.5 | 0.4M NaCl, .0022% Triton X-100 |
| 230–262 | 2.0 | 0.1M NaPhosphate, pH 6.5 | 0.4M NaCl, .0022% Triton X-100 |
| 1357–1407 | 2.0 | 0.1M Boric Acid, pH 9.0 | 0.4M NaCl, .0022% Triton X-100 |
| 1418–1457 | 2.0 | 0.1M Boric Acid, pH 9.0 | 0.4M NaCl, .0022% Triton X-100 |
| 1569–1593 | 3.0 | 0.1M Tris/HCl, pH 8.5 | 0.5M NaCl, .0022% Triton X-100 |
| 1899–1930 | 2.0 | 0.1M Tris/HCl, pH 8.5 | 0.5M NaCl, .0022% Triton X-100 |
| 1192–1240 | 2.0 | 0.1M Boric Acid, pH 9.0 | 0.4M NaCl, .0022% Triton X-100 |
| 1223–1240 | 5.0 | 0.1M Boric Acid, pH 9.0 | 0.4M NaCl, .0022% Triton X-100 |
| 1684–1750 | 1.0 | 0.1M Boric Acid, pH 10.0 | 0.4M NaCl, .0022% Triton X-100 |
| 1689–1805 | 1.0 | 0.1M Boric Acid, pH 10.0 | 0.4M NaCl, .0022% Triton X-100 |
| 1694–1735 | 3.0 | 0.1M Tris/HCl, pH 8.5 | 0.5M NaCl, .0022% Triton X-100 |
| 1866–1930 | 0.75 | 0.1M Tris/HCl, pH 8.5 | 0.5M NaCl, .0022% Triton X-100 |
| 380–436 | 3.0 | 0.1M Tris/HCl, pH 8.5 | 0.9% NaCl |
| 447–483 | 3.0 | | |
| 643–683 | 3.0 | 0.1M Tris/HCl, pH 8.5 | 0.5M NaCl, .0022% Triton X-100 |
| 2302–2352 | 3.0 | 0.1M Borate | 0.4M NaCl, .0022% Triton X-100 |
| p380JH1 | 5.0 | 0.1M Borate, pH 10.0 | 0.4M NaCl, .0022% Triton X-100 |
| p380J | 5.0 | 0.1M Borate, pH 10.0 | 0.4M NaCl, .0022% Triton X-100 |
| p408J | 5.0 | 0.1M Borate, pH 10.0 | 0.9% NaCl |

TABLE 1

| CHIRON UPDATE | GENOMIC REGION | SAMPLE A00642 DILUTION | RESULT | SAMPLE #401 DILUTION | RESULT | SAMPLE #423 DILUTION | RESULT |
|---|---|---|---|---|---|---|---|
| 1694–1735 | C-100 | 1:800 | POS. | 1:40 | POS. | 1:20 | POS. |
| 1866–1930 | C-100 | 1:100 | POS. | — | — | — | — |
| 1689–1805 | C-100 | 1:500 | POS. | 1:40 | POS. | 1:20 | POS. |
| 1684–1750 | C-100 | 1:500 | POS. | 1:40 | POS. | 1:20 | POS. |
| 1899–1930 | C-100 | 1:50 | POS. | 1:40 | POS. | 1:20 | NEG. |
| 1192–1240 | 33 C | 1:800 | POS. | 1:40 | POS. | 1:20 | POS. |
| 1223–1240 | 33 C | 1:200 | POS. | 1:40 | POS. | 1:20 | POS. |
| 1–75 | Putative Core | 1:100 | POS. | 1:40 | POS. | 1:20 | POS. |
| 35–75 | Putative Core | 1:50 | NEG. | 1:40 | NEG. | 1:20 | POS. |
| 99–126 | Putative Core | 1:50 | NEG. | 1:40 | NEG. | 1:20 | POS. |
| 1569–1593 | C-100 | 1:25 | NEG. | 1:40 | NEG. | 1:20 | NEG. |
| 1357–1407 | 33 C | 1:25 | NEG. | 1:40 | NEG. | 1:20 | NEG. |
| 1418–1457 | 33 C | 1:25 | NEG. | 1:40 | NEG. | 1:20 | NEG. |
| 195–262 | Putative Core/ Envelope | 1:50 | NEG. | 1:40 | NEG. | 1:20 | NEG. |
| 230–262 | Putative Core/ Envelope | 1:25 | NEG. | 1:40 | NEG. | 1:20 | NEG. |

A sample is considered positive if the absorbance at 492 nm ≥ 4X absorbance value of the negative control (S/N ≥ 4.0).
A00642 Human plasma sample convalescent from NANB (HCV) Hepatitis. Patient was clinically diagnosed with NANB and was negative for HBV and HAV markers.
401 Human paid plasma donor positive by screening assays based on C100-3. No known clinical history.
423 Human paid plasma donor positive by screening assays based on C100-3. No known clinical history.

TABLE 3

```
p1
                   5                      10                     15                     20
Met Ser Thr Asn Pro Lys Pro Gln Lys Lys Asn Lys Arg Asn Thr Asn Arg Arg Pro Gln
ATG TCT ACC AAC CCG AAA CCG CAG AAA AAA AAC AAA CGT AAC ACC AAC CGT CGT CCG CAC
                  25                      30                     35                     40
Asp Val Lys Phe Pro Gly Gly Gly Gln Ile Val Gly Gly Val Tyr Leu Leu Pro Arg Arg
GAC GTT AAA TTC CCG GGT GGT GGT CAG ATC GTT GGT GGT GTT TAC CTG CTG CCG CGT CGT
                  45                      50                     55                     60
Gly Pro Arg Leu Gly Val Arg Ala Thr Arg Lys Thr Ser Glu Arg Ser Gln Pro Arg Gly
GGT CCG CGT CTG GGT GTT CGT GCT ACC CGT AAA ACC TCT GAA CGT TCT CAG CCG CGT GGT
                  65                      70                     75
Arg Arg Gln Pro Ile Pro Lys Ala Arg Arg Pro Glu Gly Arg Thr
CGT CGT CAG CCG ATC CCG AAA GCT CGT CGT CCG GAA GGT CGT ACC
p1223
                   5                      10                     15
Phe Gln Val Ala His Leu His Ala Pro Thr Gly Ser Gly Lys Ser Thr Lys Val
```

TABLE 3-continued

```
TTC CAG GTT GCT CAC CTG CAC GCT CCG ACC GGT TCT GGT AAA TCT ACC AAA GTT
p1684
              5                   10                  15                  20
Gly Arg Val Val Leu Ser Gly Lys Pro Ala Ile Ile Pro Asp Arg Glu Val Leu Tyr Arg
GGT CGT GTT GTT CTG TCT GGT AAA CCG GCT ATC ATC CCG GAC CGT GAA GTT CTG TAC CGT
              25                  30                  35                  40
Glu Phe Asp Glu Met Glu Glu Cys Ser Gln His Leu Pro Tyr Ile Glu Gln Gly Met Met
GAA TTC GAC GAA ATG GAA GAA TGC TCT CAG CAC CTG CCG TAC ATC GAA CAG GGT ATG ATG
              45                  50                  55                  60
Leu Ala Glu Gln Phe Lys Gln Lys Ala Leu Gly Leu Leu Gln Thr Ala Ser Arg Gln Ala
CTG GCT GAA CAG TTC AAA CAG AAA GCT CTG GGT CTG CTG CAG ACC GCT TCT CGT CAG GCT
              65
Glu Val Ile Ala Pro Ala Val
GAA GTT ATC GCT CCG GCT GTT
```

TABLE 6

COMPARISON OF p1689 RESULTS WITH HCV SCREENING ASSAY RESULTS ON NANB PANEL II (H. ALTER, NIH).

| | C100-3 | | | ORTHO |
|---|---|---|---|---|
| SAMPLE | MANUAL S/CO | MACHINE S/CO | C100-3 S/CO | p1689 EIA S/CO |
| 1 | >5.88 | >6.47 | >6.38 | >8.33 |
| 2 | 0.63 | 0.93 | 0.27 | 0.45 |
| 3 | >5.88 | >6.47 | >6.38 | >8.33 |
| 4 | >5.88 | >6.47 | >6.38 | >8.33 |
| 5 | 0.43 | 0.35 | 0.16 | 0.43 |
| 6 | >5.88 | >6.47 | >6.38 | >8.33 |
| 7 | 0.46 | 0.73 | 0.36 | 0.32 |
| 8 | 0.41 | 0.50 | 0.32 | 0.38 |
| 9 | 1.87 | 2.21 | 0.91 | 2.84 |
| 10 | 0.35 | 0.41 | 0.32 | 0.30 |
| 11 | 0.48 | 0.45 | 0.27 | 0.46 |
| 12 | 0.32 | 0.41 | 0.17 | 0.39 |
| 13 | 0.48 | 0.69 | 0.32 | 0.51 |
| 14 | 0.37 | 0.40 | 0.19 | 0.32 |
| 15 | >5.88 | >6.47 | >6.38 | >8.33 |
| 16 | >5.88 | >6.47 | >6.38 | >8.33 |
| 17 | 0.34 | 0.40 | 0.20 | 0.44 |
| 18 | 3.01 | 3.68 | 0.68 | 6.80 |
| 19 | 0.74 | 0.61 | 0.53 | 0.71 |
| 20 | 0.53 | 0.59 | 0.28 | 0.33 |
| 21 | >5.88 | >6.47 | >6.38 | >8.33 |
| 22 | 0.24 | 0.26 | 0.20 | 0.23 |
| 23 | >5.88 | >6.47 | >6.38 | >8.33 |
| 24 | 0.69 | 0.64 | 0.53 | 0.70 |
| 25 | 0.50 | 0.60 | 0.49 | 0.40 |
| 26 | 3.41 | 4.11 | 0.77 | 6.61 |
| 27 | 0.62 | 0.74 | 0.30 | 0.65 |
| 28 | 0.61 | 0.77 | 0.08 | 0.47 |
| 29 | 0.34 | 0.42 | 0.13 | 0.33 |
| 30 | 1.58 | 2.40 | 1.26 | 2.65 |
| 31 | 0.32 | 0.35 | 0.22 | 0.37 |
| 32 | >5.88 | >6.47 | >6.38 | >8.33 |
| 33 | 0.45 | 0.48 | 0.24 | 0.45 |
| 34 | >5.88 | >6.47 | >6.38 | >8.33 |
| 35 | >5.88 | >6.47 | >6.38 | >8.33 |
| 36 | 0.37 | 0.38 | 0.21 | 0.40 |
| 37 | 0.40 | 0.46 | 0.24 | 0.52 |
| 38 | >5.88 | >6.47 | >6.38 | >8.33 |
| 39 | 0.40 | 0.49 | 0.30 | 0.46 |
| 40 | 0.53 | 0.59 | 0.30 | 0.56 |
| 41 | 0.41 | 0.23 | 0.15 | 0.32 |
| 42 | 0.52 | 0.56 | 0.38 | 0.60 |
| 43 | 0.28 | 0.30 | 0.38 | 0.33 |
| 44 | 0.44 | 0.57 | 0.35 | 0.53 |

TABLE 7

NET REFLECTANCE DENSITY (D)

| Sample | p1223 | p1684 | p1689 | p1694 | p1866 | p1223 | p1684 | p1689 | p1694 | p1866 |
|---|---|---|---|---|---|---|---|---|---|---|
| Neg Ctrl | −.0051 | −.0042 | .0047 | .0012 | .0134 | − | − | − | − | − |
| | −.004 | .0004 | .0068 | .0000 | .0119 | − | − | − | − | − |
| Sample 00642 (1:100) | .0011 | .0281 | .4401 | .0748 | .1444 | − | + | + | + | + |
| | .0002 | .0368 | .4552 | .0853 | .1564 | − | + | + | + | + |
| Sample 423 (1:40) | .0073 | .1501 | 1.5389 | .1922 | .0325 | − | + | ++ | + | + |
| Sample ALT27 | .3040 | 10.40 | 29.64 | 13.00 | 7.450 | + | ++ | +++ | ++ | ++ |
| | .1469 | 9.619 | 30.20 | 13.26 | 7.887 | + | ++ | +++ | ++ | ++ |

+/− Values Based on S/N
− Dr/Bkg < 2.5
+ 2.5 < Dr/Bkg < 100
++ 100 < Dr/Bkg < 1000
+++ Dr/Bkg > 1000

TABLE 11

AMINO ACID SEQUENCE OF PEPTIDES SELECTED FROM THE NS1 REGION OF HCV GENOME (A.A. 600–720) BASED ON PEPSCAN ANALYSIS

| A.A. NO. OF HCV GENOME | PEPTIDE SEQUENCE |
|---|---|
| 607–627 | CLVDYPYRLWHYPCTINYTIF |
| 643–663 | ACNWTRGERCDLEDRDRSELSY |
| 666–683 | LLTTTQWQVLPCSFTTLPY |
| 691–714 | HLHQNIVDVQYLYGVGSSIASWAI |

TABLE 12

REACTIVITY OF A PANEL OF HCV SEROPOSITIVE SAMPLES WITH NS1 PEPTIDES BY MICROTITER EIA

| SAMPLE ID* | PEPTIDES SELECTED FROM NS1 REGION (A.A. NUMBERS) | | | |
|---|---|---|---|---|
| | 607–627 | 643–663 | 666–683 | 691–714 |
| 15 | − | − | + | − |
| 22 | − | − | − | − |
| 23 | − | − | − | − |
| 24 | +/− | − | − | − |
| 25 | +/− | − | − | − |
| 32 | +/− | + | + | − |
| 36 | − | − | − | − |
| 46 | − | − | − | − |
| 50 | − | − | − | − |
| 65 | − | − | − | − |
| 70 | − | + | + | − |
| 71 | − | − | + | − |
| 75 | − | − | − | − |
| 89 | − | ++ | − | + |
| 95 | − | ++ | ++ | + |
| 100 | − | ++ | − | − |
| 102 | − | − | − | − |
| 108 | − | − | − | − |
| 130 | − | − | + | − |
| 137 | − | − | − | − |
| LG | + | ++ | +++ | + |
| 301060 | − | ++ | +++ | + |
| PB3178 | ++ | + | +++ | + |
| PB3180 | ++ | + | +++ | ++ |
| 300423 | ++ | − | +++ | + |
| % POSITIVE | 16 | 36 | 44 | 27 |

*ALL SAMPLES SHOWED THE PRESENCE OF ANTIBODIES TO HEPATITIS C VIRUS BY EIA AS WELL AS WESTERN BLOT ANALYSIS.

---

We claim:

1. An assay for detecting the presence of an antibody immunologically reactive with a Hepatitis C Virus (HCV) antigen in a fluid sample comprising:
   (a) contacting the sample with a polypeptide selected from the group consisting of p380-JH1, p380-J, p380.LG, and p408, said polypeptide containing at least one epitope of an HCV antigen, under conditions suitable for complexing the antibody with the polypeptide; and
   (b) detecting the antibody-polypeptide complex as an indication of the presence of an antibody immunologically reactive with HCV antigen in said fluid sample.

2. The assay of claim 1 wherein the polypeptide is bound to a solid support.

3. The assay of claim 1 wherein said polypeptide of said step (a) further comprises a detectable label selected from the group consisting of an enzyme, a radioisotope, a fluorescent reagent, a luminescent reagent and a chemiluminescent reagent.

4. A combination assay for the presence of an antibody immunologically reactive with an Hepatitis C Virus (HCV) antigen in a fluid sample comprising:
   (a) contacting the sample with a solid support having bound thereto at least one polypeptide selected from the group consisting of p380-JH1, p380-J, p-380.LG, and p408, said polypeptide containing at least one epitope of an HCV antigen, under conditions suitable for complexing the antibody with the polypeptide; and
   (b) detecting the antibody-polypeptide complex as an indication of the presence of an antibody immunologically reactive with HCV antigen in said fluid sample.

5. The assay of claim 4 wherein the solid support is a polystyrene bead.

6. The assay of claim 4 wherein said polypeptide of said step (a) further comprises a detectable label selected from the group consisting of an enzyme, a radioisotope, a fluorescent reagent, a luminescent reagent and a chemiluminescent reagent.

7. A confirmatory assay for detecting the presence of an antibody in a fluid sample, the assay comprising the steps of:
   (a) providing first and second immunologically equivalent aliquots of a fluid sample, wherein the fluid sample may contain at least one Hepatitis C Virus (HCV) antibody;
   (b) contacting the first aliquot with a first polypeptide selected from the group consisting of p380-JH1, p380-J, p-380.LG and p408, under conditions suitable for complexing the antibody with the polypeptide to provide a first antibody-antigen complex, wherein said first polypeptide contains at least one epitope of an HCV antigen;
   (c) detecting the first antibody-antigen complex;
   (d) contacting the second aliquot with a second polypeptide selected from-the group consisting of p380-JH1, p380-J, p380.LG, and p408 under conditions suitable to form a second antibody-antigen complex, wherein the first and second selected polypeptides are not identical; and
   (e) detecting the second antibody-antigen complex, wherein the detection of the first and second antibody-antigen complexes is indicative of the presence of an antibody in the fluid sample.

8. The assay of claim 7 wherein the polypeptides are bound to a solid support.

9. The assay of claim 6 wherein said solid support is a polystyrene bead.

10. An immunodot assay for identifying the presence of an antibody immunologically reactive with an HCV antigen in a fluid sample comprising:

concurrently contacting the sample with at least two polypeptides selected from the group consisting of p380-JH1, p380-J, p-380.LG, and p408, each containing distinct epitopes of an HCV antigen and coated onto a solid support, under conditions suitable for complexing the antibody with the polypeptides; and detecting the antibody-polypeptide by reacting the complex with color-producing reagents.

11. A competition assay for identifying the presence of an antibody immunologically reactive with an HCV antigen in a fluid sample wherein the sample is used to prepare first and second immunologically equivalent aliquots comprising:

a first step comprising contacting a first aliquot of test sample with a solid support coated with a polypeptide selected from the group consisting of p380, p380-JH1, p380.LG, and p408, said polypeptide containing at least one epitope of an HCV antigen, under conditions suitable for complexing with the antibody to form a detectable antibody-polypeptide complex and obtaining a result by detecting said complex;

a second step comprising contacting the second aliquot with an unbound solution of said polypeptide, and subsequently contacting said second aliquot with a solid support coated with said polypeptide under conditions suitable for complexing with the antibody to form a detectable antibody-polypeptide complex and obtaining a result by detecting antibody bound to said solid support; and comparing the result obtained during said first step with the result obtained during said second step as an indication of the presence of antibody in said sample.

12. An immunoassay kit comprising:

a polypeptide selected from the group consisting of p380-JH1, p380-J, p380.LG, and p408, said polypeptide containing at least one epitope of an HCV antigen;

one or more sample preparation reagents; and one or more detection and signal producing reagents.

13. The kit of claim 12 wherein the polypeptide is coated on a solid support.

14. The immunoassay kit of claim 12 wherein said detection reagent further comprises a detectable label selected from the group consisting of an enzyme, a radioisotope, a fluorescent reagent, a luminescent reagent and a chemiluminescent reagent.

* * * * *